(12) United States Patent
Benary et al.

(10) Patent No.: US 9,597,204 B2
(45) Date of Patent: Mar. 21, 2017

(54) BRANCHED STENT-GRAFT SYSTEM

(71) Applicant: ENDOSPAN LTD., Herzilyia Pituach (IL)

(72) Inventors: Raphael Benary, Tel Aviv (IL); Alon Shalev, Ra'anana (IL); Nir Shalom Nae, Ra'anana (IL)

(73) Assignee: ENDOSPAN LTD., Herzilyia Pituach (IL)

( * ) Notice: Subject to any disclaimer, the term of this patent is extended or adjusted under 35 U.S.C. 154(b) by 96 days.

(21) Appl. No.: 14/362,194

(22) PCT Filed: Dec. 4, 2012

(86) PCT No.: PCT/IL2012/050506
§ 371 (c)(1),
(2) Date: Jun. 2, 2014

(87) PCT Pub. No.: WO2013/084235
PCT Pub. Date: Jun. 13, 2013

(65) Prior Publication Data
US 2014/0350658 A1 Nov. 27, 2014

Related U.S. Application Data

(60) Provisional application No. 61/566,654, filed on Dec. 4, 2011.

(51) Int. Cl.
*A61F 2/07* (2013.01)
*A61F 2/82* (2013.01)
(Continued)

(52) U.S. Cl.
CPC .................. *A61F 2/82* (2013.01); *A61F 2/07* (2013.01); *A61F 2/856* (2013.01); *A61F 2/89* (2013.01);
(Continued)

(58) Field of Classification Search
CPC .................. A61F 2/07; A61F 2002/075; A61F 2002/061; A61F 2/89; A61F 2002/067;
(Continued)

(56) References Cited

U.S. PATENT DOCUMENTS

| 4,180,613 A | 12/1979 | Vassiliou |
| 4,355,426 A | 10/1982 | MacGregor |

(Continued)

FOREIGN PATENT DOCUMENTS

| CA | 2497704 | 3/2004 |
| CN | 2453960 | 10/2001 |

(Continued)

OTHER PUBLICATIONS

Scurr, James; McWilliams, Richard. Fenestrated Aortic Stent Grafts. Seminars in Interventional Radiology vol. 24, No. 2. (2007).*

(Continued)

*Primary Examiner* — Christian Sevilla
*Assistant Examiner* — Seema Mathew
(74) *Attorney, Agent, or Firm* — Sughrue Mion, PLLC

(57) ABSTRACT

An endovascular stent-graft (10) includes a generally tubular hourglass-shaped body (22), which is configured to assume a radially-compressed delivery configuration and a radially-expanded deployment configuration. The hourglass-shaped body (22) includes a flexible stent member (26), which includes a plurality of structural stent elements (28); and a tubular fluid flow guide (24), which includes a fabric (29), and is attached to the structural stent elements (28). The hourglass-shaped body (22) is shaped so as to define a narrow waist portion (32) longitudinally surrounded by and adjacent to wider first and second longitudinal portions (30, 34). The fabric (29) along the waist portion (32) is shaped so (Continued)

as to define at least first and second lateral apertures (36, 38). Other embodiments are also described.

29 Claims, 17 Drawing Sheets

(51) Int. Cl.
  *A61F 2/856* (2013.01)
  *A61F 2/915* (2013.01)
  *A61F 2/06* (2013.01)
  *A61F 2/89* (2013.01)
  *A61F 2/95* (2013.01)

(52) U.S. Cl.
  CPC ......... *A61F 2/915* (2013.01); *A61F 2002/061* (2013.01); *A61F 2002/067* (2013.01); *A61F 2002/075* (2013.01); *A61F 2002/91508* (2013.01); *A61F 2002/9511* (2013.01); *A61F 2220/0075* (2013.01); *A61F 2230/0078* (2013.01); *A61F 2250/0039* (2013.01); *A61F 2250/0098* (2013.01)

(58) Field of Classification Search
  CPC .............. A61F 2/856; A61F 2220/0075; A61F 2002/9511; A61F 2/954; A61F 2/90; A61F 2230/0054; A61F 2/95; A61F 2/958; A61F 2/064; A61F 2/852; A61F 2/962; A61F 2/06; A61F 2/915; A61F 2002/8483; A61F 2002/8486; A61F 2/2418; A61F 2/848; A61F 2/86; A61F 2/88; A61F 2/91
  See application file for complete search history.

(56) References Cited

U.S. PATENT DOCUMENTS

| | | |
|---|---|---|
| 4,505,767 A | 3/1985 | Quin |
| 4,562,596 A | 1/1986 | Kornberg |
| 4,577,631 A | 3/1986 | Kreamer |
| 4,617,932 A | 10/1986 | Kornberg |
| 4,665,906 A | 5/1987 | Jervis |
| 4,739,762 A | 4/1988 | Palmaz |
| 4,787,899 A | 11/1988 | Lazarus |
| 4,816,339 A | 3/1989 | Tu et al. |
| 4,878,906 A | 11/1989 | Lindemann et al. |
| 4,886,062 A | 12/1989 | Wiktor |
| 4,938,740 A | 7/1990 | Melbin |
| 4,969,458 A | 11/1990 | Wiktor |
| 5,042,707 A | 8/1991 | Taheri |
| 5,064,435 A | 11/1991 | Porter |
| 5,104,404 A | 4/1992 | Wolff |
| 5,122,136 A | 6/1992 | Guglielmi et al. |
| 5,133,732 A | 7/1992 | Wiktor |
| 5,192,256 A | 3/1993 | Ryan |
| 5,192,286 A | 3/1993 | Phan et al. |
| 5,234,448 A | 8/1993 | Wholey et al. |
| 5,383,926 A | 1/1995 | Lock et al. |
| 5,425,739 A | 6/1995 | Jessen |
| 5,456,694 A | 10/1995 | Marin et al. |
| 5,486,183 A | 1/1996 | Middleman et al. |
| 5,507,769 A | 4/1996 | Marin et al. |
| 5,509,923 A | 4/1996 | Middleman et al. |
| 5,522,880 A | 6/1996 | Barone et al. |
| 5,527,322 A | 6/1996 | Klein et al. |
| 5,549,662 A | 8/1996 | Fordenbacher |
| 5,554,181 A | 9/1996 | Das |
| 5,556,413 A | 9/1996 | Lam |
| 5,562,724 A | 10/1996 | Vorwerk et al. |
| 5,575,818 A | 11/1996 | Pinchuck |
| 5,607,445 A | 3/1997 | Summers |
| 5,613,974 A | 3/1997 | Andreas et al. |
| 5,632,746 A | 5/1997 | Middleman et al. |
| 5,632,763 A | 5/1997 | Glastra |
| 5,632,772 A | 5/1997 | Alcime et al. |
| 5,639,278 A | 6/1997 | Dereume et al. |
| 5,643,340 A | 7/1997 | Nunokawa |
| 5,653,743 A | 8/1997 | Martin |
| 5,676,696 A | 10/1997 | Marcade |
| 5,676,697 A | 10/1997 | McDonald |
| 5,693,084 A | 12/1997 | Chuter |
| 5,728,134 A | 3/1998 | Barak |
| 5,749,879 A | 5/1998 | Middleman et al. |
| 5,755,770 A | 5/1998 | Ravenscroft |
| 5,755,771 A | 5/1998 | Penn et al. |
| 5,755,777 A | 5/1998 | Chuter |
| 5,755,781 A | 5/1998 | Jayaraman |
| 5,769,882 A | 6/1998 | Fogarty et al. |
| 5,769,884 A | 6/1998 | Solovay |
| 5,782,903 A | 7/1998 | Wiktor |
| 5,782,906 A | 7/1998 | Marshall et al. |
| 5,824,040 A | 10/1998 | Cox et al. |
| 5,824,055 A | 10/1998 | Spiridigliozzi et al. |
| 5,827,321 A | 10/1998 | Roubin et al. |
| 5,843,170 A | 12/1998 | Ahn |
| 5,855,600 A | 1/1999 | Alt |
| 5,860,991 A | 1/1999 | Klein et al. |
| 5,876,432 A | 3/1999 | Lau et al. |
| 5,906,641 A | 5/1999 | Thompson et al. |
| 5,921,994 A | 7/1999 | Andreas et al. |
| 5,925,076 A | 7/1999 | Inoue |
| 5,944,750 A | 8/1999 | Tanner et al. |
| 5,948,018 A | 9/1999 | Dereume et al. |
| 5,968,091 A | 10/1999 | Pinchuk et al. |
| 5,980,552 A | 11/1999 | Pinchasik et al. |
| 5,984,955 A | 11/1999 | Wisselink |
| 6,015,431 A | 1/2000 | Thornton et al. |
| 6,016,810 A | 1/2000 | Ravenscroft |
| 6,030,414 A | 2/2000 | Taheri |
| 6,033,435 A | 3/2000 | Penn et al. |
| 6,036,723 A | 3/2000 | Anidjar et al. |
| 6,036,725 A | 3/2000 | Avellanet |
| 6,049,824 A | 4/2000 | Simonin |
| 6,051,021 A | 4/2000 | Frid |
| 6,059,824 A | 5/2000 | Taheri |
| 6,099,497 A | 8/2000 | Adams et al. |
| 6,099,548 A | 8/2000 | Taheri |
| 6,117,145 A | 9/2000 | Wood et al. |
| 6,129,738 A | 10/2000 | Lashinski et al. |
| 6,132,457 A | 10/2000 | Chobotov |
| 6,156,064 A | 12/2000 | Chouinard |
| 6,159,228 A | 12/2000 | Frid et al. |
| 6,176,875 B1 | 1/2001 | Lenker et al. |
| 6,179,878 B1 | 1/2001 | Duerig et al. |
| 6,200,339 B1 | 3/2001 | Leschinsky et al. |
| 6,206,893 B1 | 3/2001 | Klein et al. |
| 6,270,524 B1 | 8/2001 | Kim |
| 6,283,991 B1 | 9/2001 | Cox et al. |
| 6,287,335 B1 | 9/2001 | Drasler et al. |
| 6,290,720 B1 | 9/2001 | Khosravi et al. |
| 6,296,661 B1 | 10/2001 | Davila et al. |
| 6,312,458 B1 | 11/2001 | Golds |
| 6,325,819 B1 | 12/2001 | Pavcnik et al. |
| 6,325,823 B1 | 12/2001 | Horzewski et al. |
| 6,344,056 B1 | 2/2002 | Dehdashtian |
| 6,395,018 B1 | 5/2002 | Castaneda |
| 6,406,420 B1 | 6/2002 | McCarthy et al. |
| 6,428,565 B1 | 8/2002 | Wisselink |
| 6,451,051 B2 | 9/2002 | Drasler et al. |
| 6,471,722 B1 | 10/2002 | Inoue |
| 6,506,211 B1 | 1/2003 | Skubitz et al. |
| 6,520,988 B1 | 2/2003 | Colombo et al. |
| 6,544,279 B1 | 4/2003 | Hopkins et al. |
| 6,576,009 B2 | 6/2003 | Ryan et al. |
| 6,613,078 B1 | 9/2003 | Barone |
| 6,635,083 B1 | 10/2003 | Cheng et al. |
| 6,645,242 B1 | 11/2003 | Quinn |
| 6,648,911 B1 | 11/2003 | Sirhan et al. |
| 6,652,567 B1 | 11/2003 | Deaton |
| 6,652,571 B1 | 11/2003 | White et al. |
| 6,656,214 B1 | 12/2003 | Fogarty et al. |
| 6,673,080 B2 | 1/2004 | Reynolds et al. |

(56) References Cited

U.S. PATENT DOCUMENTS

| | | |
|---|---|---|
| 6,692,520 B1 | 2/2004 | Gambale et al. |
| 6,695,833 B1 | 2/2004 | Frantzen |
| 6,695,875 B2 | 2/2004 | Stelter et al. |
| 6,699,277 B1 | 3/2004 | Freidberg et al. |
| 6,716,238 B2 | 4/2004 | Elliott |
| 6,733,523 B2 | 5/2004 | Shaolian et al. |
| 6,743,195 B2 | 6/2004 | Zucker |
| 6,752,826 B2 | 6/2004 | Holloway et al. |
| 6,776,794 B1 | 8/2004 | Hong et al. |
| 6,808,534 B1 | 10/2004 | Escano |
| 6,814,749 B2 | 11/2004 | Cox et al. |
| 6,814,752 B1 | 11/2004 | Chuter |
| 6,824,560 B2 | 11/2004 | Pelton |
| 6,843,803 B2 | 1/2005 | Ryan et al. |
| 6,846,321 B2 | 1/2005 | Zucker |
| 6,860,900 B2 | 3/2005 | Clerc et al. |
| 6,907,285 B2 | 6/2005 | Denker et al. |
| 6,908,477 B2 | 6/2005 | McGuckin, Jr. et al. |
| 6,929,660 B1 | 8/2005 | Ainsworth et al. |
| 6,942,691 B1 | 9/2005 | Chuter |
| 6,964,679 B1 | 11/2005 | Marcade et al. |
| 6,986,774 B2 | 1/2006 | Middleman et al. |
| 7,008,441 B2 | 3/2006 | Zucker |
| 7,018,400 B2 | 3/2006 | Lashinski et al. |
| 7,022,131 B1 | 4/2006 | Derowe et al. |
| 7,044,962 B2 | 5/2006 | Elliott |
| 7,105,015 B2 | 9/2006 | Goshgarian |
| 7,105,020 B2 | 9/2006 | Greenberg et al. |
| 7,112,217 B1 | 9/2006 | Kugler et al. |
| 7,115,127 B2 | 10/2006 | Lindenbaum et al. |
| 7,122,052 B2 | 10/2006 | Greenhalgh |
| 7,131,991 B2 | 11/2006 | Zarins et al. |
| 7,144,421 B2 | 12/2006 | Carpenter et al. |
| 7,160,318 B2 | 1/2007 | Greenberg et al. |
| 7,175,651 B2 | 2/2007 | Kerr |
| 7,198,638 B2 | 4/2007 | Dong |
| 7,201,772 B2 | 4/2007 | Schwammenthal et al. |
| 7,220,274 B1 | 5/2007 | Quinn |
| 7,223,266 B2 | 5/2007 | Lindenbaum et al. |
| 7,270,675 B2 | 9/2007 | Chun et al. |
| 7,279,003 B2 | 10/2007 | Berra et al. |
| 7,294,145 B2 | 11/2007 | Ward |
| 7,294,147 B2 | 11/2007 | Hartley |
| 7,306,623 B2 | 12/2007 | Watson |
| 7,341,598 B2 | 3/2008 | Davidson et al. |
| 7,393,357 B2 | 7/2008 | Stelter et al. |
| 7,396,363 B2 | 7/2008 | Frid |
| 7,407,509 B2 | 8/2008 | Greenberg et al. |
| 7,413,573 B2 | 8/2008 | Hartley et al. |
| 7,425,219 B2 | 9/2008 | Quadri |
| 7,429,269 B2 | 9/2008 | Schwammenthal et al. |
| 7,438,721 B2 | 10/2008 | Doig et al. |
| 7,442,204 B2 | 10/2008 | Schwammenthal et al. |
| 7,473,272 B2 | 1/2009 | Pryor |
| 7,491,231 B2 | 2/2009 | Nazzaro et al. |
| 7,537,606 B2 | 5/2009 | Hartley et al. |
| 7,537,609 B2 | 5/2009 | Davidson et al. |
| 7,540,881 B2 | 6/2009 | Meyer et al. |
| 7,544,160 B2 | 6/2009 | Gross |
| 7,575,590 B2 | 8/2009 | Watson |
| 7,637,939 B2 | 12/2009 | Tischler |
| 7,645,298 B2 | 1/2010 | Hartley et al. |
| 7,655,036 B2 | 2/2010 | Goodson |
| 7,662,161 B2 | 2/2010 | Briganti et al. |
| 7,662,168 B2 | 2/2010 | McGuckin, Jr. et al. |
| 7,670,369 B2 | 3/2010 | Schaeffer |
| 7,678,141 B2 | 3/2010 | Greenan et al. |
| 7,699,885 B2 | 4/2010 | Leonhardt et al. |
| 7,708,704 B2 | 5/2010 | Mitelberg et al. |
| 7,722,626 B2 | 5/2010 | Middleman et al. |
| 7,731,732 B2 | 6/2010 | Ken |
| 7,766,955 B2 | 8/2010 | Vardi et al. |
| 7,771,465 B2 | 8/2010 | Zukowski |
| 7,789,903 B2 | 9/2010 | Spiridigliozzi et al. |
| 7,803,178 B2 | 9/2010 | Whirley et al. |
| 7,806,923 B2 | 10/2010 | Moloney |
| 7,815,673 B2 | 10/2010 | Bloom et al. |
| 7,833,259 B2 | 11/2010 | Boatman |
| 7,846,194 B2 | 12/2010 | Hartley et al. |
| 7,850,725 B2 | 12/2010 | Vardi et al. |
| 7,867,270 B2 | 1/2011 | Hartley et al. |
| 7,887,575 B2 | 2/2011 | Kujawski |
| 7,914,572 B2 | 3/2011 | Hartley et al. |
| 7,955,373 B2 | 6/2011 | Sowinski et al. |
| 7,955,374 B2 | 6/2011 | Erickson et al. |
| 7,959,662 B2 | 6/2011 | Erbel et al. |
| 7,959,669 B2 | 6/2011 | Chalekian et al. |
| 7,998,186 B2 | 8/2011 | Hartley |
| 7,998,187 B2 | 8/2011 | Hartley et al. |
| 8,012,193 B2 | 9/2011 | Hartley et al. |
| 8,021,412 B2 | 9/2011 | Hartley et al. |
| 8,021,418 B2 | 9/2011 | Gerberding et al. |
| 8,021,419 B2 | 9/2011 | Hartley et al. |
| 8,043,365 B2 | 10/2011 | Thramann |
| 8,048,139 B2 | 11/2011 | Frid et al. |
| 8,048,140 B2 | 11/2011 | Purdy |
| 8,048,147 B2 | 11/2011 | Adams |
| 8,052,736 B2 | 11/2011 | Doig et al. |
| 8,052,741 B2 | 11/2011 | Bruszewski et al. |
| 8,066,755 B2 | 11/2011 | Zacharias et al. |
| 8,080,053 B2 | 12/2011 | Satasiya et al. |
| 8,100,960 B2 | 1/2012 | Bruszewski |
| 8,118,854 B2 | 2/2012 | Bowe |
| 8,133,267 B2 | 3/2012 | Leonhardt et al. |
| 8,157,810 B2 | 4/2012 | Case et al. |
| 8,167,926 B2 | 5/2012 | Hartley et al. |
| 8,172,892 B2 | 5/2012 | Chuter et al. |
| 8,172,895 B2 | 5/2012 | Anderson et al. |
| 8,197,475 B2 | 6/2012 | Bruszewski et al. |
| 8,197,533 B2 | 6/2012 | Kujawski |
| 8,211,158 B2 | 7/2012 | Wolf |
| 8,216,298 B2 | 7/2012 | Wright et al. |
| 8,221,494 B2 | 7/2012 | Schreck et al. |
| 8,226,706 B2 | 7/2012 | Hartley et al. |
| 8,236,040 B2 | 8/2012 | Mayberry et al. |
| 8,251,963 B2 | 8/2012 | Chin et al. |
| 8,257,423 B2 | 9/2012 | Kerr |
| 8,262,719 B2 | 9/2012 | Erickson et al. |
| 8,273,115 B2 | 9/2012 | Hamer et al. |
| 8,287,586 B2 | 10/2012 | Schaeffer et al. |
| 8,292,885 B2 | 10/2012 | Bruszewski et al. |
| 8,292,941 B2 | 10/2012 | Muzslay |
| 8,292,949 B2 | 10/2012 | Berra et al. |
| 8,292,951 B2 | 10/2012 | Muzslay |
| 8,333,800 B2 | 12/2012 | Bruszewski et al. |
| 8,337,546 B2 | 12/2012 | Bruszewski |
| 8,353,898 B2 | 1/2013 | Lutze et al. |
| 8,357,192 B2 | 1/2013 | Mayberry et al. |
| 8,361,134 B2 | 1/2013 | Hartley et al. |
| 8,394,136 B2 | 3/2013 | Hartley et al. |
| 8,425,585 B2 | 4/2013 | Melsheimer et al. |
| 8,470,018 B2 | 6/2013 | Hartley et al. |
| 8,475,513 B2 | 7/2013 | Sithian |
| 8,480,726 B2 | 7/2013 | Cunningham et al. |
| 8,486,131 B2 | 7/2013 | Shalev |
| 8,491,646 B2 | 7/2013 | Schreck |
| 8,506,622 B2 | 8/2013 | Bruszewski et al. |
| 8,728,148 B2 * | 5/2014 | Roeder ............... A61F 2/07 623/1.11 |
| 8,808,355 B2 * | 8/2014 | Barrand ............... A61F 2/856 623/1.13 |
| 8,968,384 B2 * | 3/2015 | Pearson ............... A61F 2/07 623/1.13 |
| 9,101,457 B2 * | 8/2015 | Benary ............... A61F 2/07 |
| 9,168,123 B2 * | 10/2015 | Barrand ............... A61F 2/07 |
| 9,254,209 B2 * | 2/2016 | Shalev ............... A61F 2/064 |
| 2001/0000188 A1 | 4/2001 | Lenker et al. |
| 2001/0004705 A1 | 6/2001 | Killion et al. |
| 2001/0014823 A1 | 8/2001 | Ressemann et al. |
| 2001/0034550 A1 | 10/2001 | Buirge et al. |
| 2001/0037142 A1 | 11/2001 | Stelter et al. |
| 2001/0044647 A1 | 11/2001 | Pinchuk et al. |
| 2001/0044651 A1 | 11/2001 | Steinke et al. |
| 2001/0044652 A1 | 11/2001 | Moore |

(56) References Cited

U.S. PATENT DOCUMENTS

| | | |
|---|---|---|
| 2001/0047198 A1 | 11/2001 | Drasler et al. |
| 2001/0049550 A1 | 12/2001 | Martin et al. |
| 2001/0053930 A1 | 12/2001 | Kugler et al. |
| 2002/0040236 A1 | 4/2002 | Lau et al. |
| 2002/0052643 A1 | 5/2002 | Wholey et al. |
| 2002/0052644 A1 | 5/2002 | Shaolian et al. |
| 2002/0072790 A1 | 6/2002 | McGuckin, Jr. et al. |
| 2002/0099438 A1 | 7/2002 | Furst |
| 2002/0099441 A1 | 7/2002 | Dehdashtian |
| 2002/0107564 A1 | 8/2002 | Cox et al. |
| 2002/0111667 A1 | 8/2002 | Girton et al. |
| 2002/0123791 A1 | 9/2002 | Harrison |
| 2002/0156495 A1 | 10/2002 | Brenneman et al. |
| 2002/0156517 A1 | 10/2002 | Perouse |
| 2002/0173809 A1 | 11/2002 | Fleischman et al. |
| 2002/0183783 A1 | 12/2002 | Shadduck |
| 2002/0193864 A1 | 12/2002 | Khosravi et al. |
| 2002/0198585 A1 | 12/2002 | Wisselink |
| 2003/0033005 A1 | 2/2003 | Houser et al. |
| 2003/0040791 A1 | 2/2003 | Oktay |
| 2003/0040804 A1* | 2/2003 | Stack .................. A61F 2/04 623/23.7 |
| 2003/0065386 A1 | 4/2003 | Weadock |
| 2003/0068296 A1 | 4/2003 | Ricci et al. |
| 2003/0074055 A1 | 4/2003 | Haverkost |
| 2003/0093145 A1 | 5/2003 | Lawrence-Brown et al. |
| 2003/0114061 A1 | 6/2003 | Matsuda et al. |
| 2003/0125796 A1 | 7/2003 | Dong |
| 2003/0130720 A1 | 7/2003 | DePalma et al. |
| 2003/0139802 A1 | 7/2003 | Wulfman et al. |
| 2003/0144725 A1 | 7/2003 | Lombardi |
| 2003/0153944 A1 | 8/2003 | Phung et al. |
| 2003/0153968 A1 | 8/2003 | Geis et al. |
| 2003/0171771 A1 | 9/2003 | Anderson et al. |
| 2003/0191523 A1 | 10/2003 | Hojeibane |
| 2003/0199967 A1 | 10/2003 | Hartley et al. |
| 2003/0199968 A1 | 10/2003 | Ainsworth et al. |
| 2003/0204236 A1 | 10/2003 | Letort |
| 2003/0204242 A1 | 10/2003 | Zarins et al. |
| 2003/0204243 A1 | 10/2003 | Shiu |
| 2003/0212449 A1 | 11/2003 | Cox |
| 2003/0233117 A1 | 12/2003 | Adams et al. |
| 2003/0236567 A1 | 12/2003 | Elliot |
| 2004/0015227 A1 | 1/2004 | Vardi et al. |
| 2004/0015229 A1 | 1/2004 | Fulkerson et al. |
| 2004/0098091 A1 | 5/2004 | Erbel et al. |
| 2004/0106972 A1 | 6/2004 | Deaton |
| 2004/0106978 A1 | 6/2004 | Greenberg et al. |
| 2004/0117003 A1 | 6/2004 | Ouriel et al. |
| 2004/0133266 A1 | 7/2004 | Clerc et al. |
| 2004/0138735 A1 | 7/2004 | Shaolian et al. |
| 2004/0162606 A1 | 8/2004 | Thompson |
| 2004/0171978 A1 | 9/2004 | Shalaby |
| 2004/0181149 A1 | 9/2004 | Langlotz et al. |
| 2004/0215319 A1 | 10/2004 | Berra et al. |
| 2004/0215320 A1 | 10/2004 | Machek |
| 2004/0215327 A1 | 10/2004 | Doig et al. |
| 2004/0215332 A1 | 10/2004 | Frid |
| 2004/0260383 A1 | 12/2004 | Stelter et al. |
| 2005/0010246 A1 | 1/2005 | Streeter et al. |
| 2005/0033406 A1* | 2/2005 | Barnhart .................. A61F 2/07 623/1.13 |
| 2005/0049678 A1 | 3/2005 | Cocks et al. |
| 2005/0065545 A1 | 3/2005 | Wallace |
| 2005/0085900 A1 | 4/2005 | Case et al. |
| 2005/0102018 A1 | 5/2005 | Carpenter et al. |
| 2005/0102021 A1 | 5/2005 | Osborne |
| 2005/0131517 A1 | 6/2005 | Hartley et al. |
| 2005/0137682 A1 | 6/2005 | Justino |
| 2005/0149166 A1 | 7/2005 | Schaeffer et al. |
| 2005/0154448 A1 | 7/2005 | Cully et al. |
| 2005/0159803 A1 | 7/2005 | Lad et al. |
| 2005/0165480 A1 | 7/2005 | Jordan et al. |
| 2005/0171598 A1 | 8/2005 | Schaeffer |
| 2005/0171599 A1 | 8/2005 | White |
| 2005/0177132 A1 | 8/2005 | Lentz et al. |
| 2005/0203606 A1 | 9/2005 | VanCamp |
| 2005/0216018 A1 | 9/2005 | Sennett |
| 2005/0222667 A1 | 10/2005 | Hunt |
| 2005/0222668 A1 | 10/2005 | Schaeffer et al. |
| 2005/0222669 A1 | 10/2005 | Purdy |
| 2005/0228480 A1 | 10/2005 | Douglas et al. |
| 2005/0234542 A1 | 10/2005 | Melsheimer |
| 2005/0266042 A1 | 12/2005 | Tseng |
| 2005/0273155 A1 | 12/2005 | Bahler et al. |
| 2005/0283188 A1 | 12/2005 | Loshakove et al. |
| 2006/0015170 A1 | 1/2006 | Jones et al. |
| 2006/0030921 A1 | 2/2006 | Chu |
| 2006/0052799 A1 | 3/2006 | Middleman et al. |
| 2006/0069426 A1 | 3/2006 | Weinberger |
| 2006/0095114 A1 | 5/2006 | Hartley et al. |
| 2006/0100684 A1 | 5/2006 | Elliott |
| 2006/0106406 A1 | 5/2006 | Weinberger |
| 2006/0116748 A1 | 6/2006 | Kaplan et al. |
| 2006/0149360 A1 | 7/2006 | Schwammenthal et al. |
| 2006/0155358 A1 | 7/2006 | LaDuca et al. |
| 2006/0155359 A1 | 7/2006 | Watson |
| 2006/0155366 A1 | 7/2006 | LaDuca et al. |
| 2006/0167476 A1 | 7/2006 | Burdulis, Jr. et al. |
| 2006/0173530 A1 | 8/2006 | Das |
| 2006/0190070 A1 | 8/2006 | Dieck et al. |
| 2006/0193892 A1 | 8/2006 | Furst et al. |
| 2006/0212113 A1 | 9/2006 | Shaolian et al. |
| 2006/0229709 A1 | 10/2006 | Morris et al. |
| 2006/0241740 A1 | 10/2006 | Vardi et al. |
| 2006/0271166 A1 | 11/2006 | Thill et al. |
| 2006/0276882 A1 | 12/2006 | Case et al. |
| 2006/0281966 A1 | 12/2006 | Peacock, III |
| 2006/1010640 | 12/2006 | Peacock, III |
| 2007/0016281 A1 | 1/2007 | Melsheimer |
| 2007/0021822 A1 | 1/2007 | Boatman |
| 2007/0027526 A1 | 2/2007 | Demetriades et al. |
| 2007/0043425 A1 | 2/2007 | Hartley et al. |
| 2007/0050011 A1 | 3/2007 | Klein et al. |
| 2007/0055326 A1 | 3/2007 | Farley et al. |
| 2007/0055350 A1 | 3/2007 | Erickson et al. |
| 2007/0055358 A1 | 3/2007 | Krolik et al. |
| 2007/0055360 A1 | 3/2007 | Hanson et al. |
| 2007/0060989 A1 | 3/2007 | Deem et al. |
| 2007/0061002 A1 | 3/2007 | Paul, Jr. et al. |
| 2007/0073373 A1 | 3/2007 | Bonsignore |
| 2007/0088425 A1 | 4/2007 | Schaeffer |
| 2007/0112344 A1 | 5/2007 | Keilman |
| 2007/0135677 A1 | 6/2007 | Miller et al. |
| 2007/0142896 A1 | 6/2007 | Anderson et al. |
| 2007/0150051 A1 | 6/2007 | Arnault De La Menardiere et al. |
| 2007/0156167 A1 | 7/2007 | Connors et al. |
| 2007/0162104 A1 | 7/2007 | Frid |
| 2007/0167898 A1 | 7/2007 | Peters et al. |
| 2007/0167955 A1 | 7/2007 | Arnault De La Menardiere et al. |
| 2007/0168013 A1 | 7/2007 | Douglas |
| 2007/0168018 A1 | 7/2007 | Amplatz et al. |
| 2007/0179598 A1 | 8/2007 | Duerig |
| 2007/0185565 A1 | 8/2007 | Schwammenthal et al. |
| 2007/0207186 A1 | 9/2007 | Scanlon et al. |
| 2007/0208410 A1 | 9/2007 | Berra et al. |
| 2007/0213805 A1 | 9/2007 | Schaeffer et al. |
| 2007/0213807 A1 | 9/2007 | Roubin et al. |
| 2007/0219610 A1 | 9/2007 | Israel |
| 2007/0219627 A1 | 9/2007 | Chu et al. |
| 2007/0225797 A1 | 9/2007 | Krivoruhko |
| 2007/0233229 A1* | 10/2007 | Berra .................. A61F 2/07 623/1.13 |
| 2007/0237973 A1 | 10/2007 | Purdy et al. |
| 2007/0244542 A1 | 10/2007 | Greenan et al. |
| 2007/0244543 A1 | 10/2007 | Mitchell |
| 2007/0244547 A1 | 10/2007 | Greenan |
| 2007/0250154 A1 | 10/2007 | Greenberg et al. |
| 2007/0255388 A1 | 11/2007 | Rudakov et al. |
| 2008/0002871 A1 | 1/2008 | Gunzert-Marx et al. |
| 2008/0015673 A1 | 1/2008 | Chuter |
| 2008/0058918 A1 | 3/2008 | Watson |
| 2008/0109058 A1 | 5/2008 | Greenberg et al. |
| 2008/0109066 A1 | 5/2008 | Quinn |

(56) References Cited

U.S. PATENT DOCUMENTS

| | | |
|---|---|---|
| 2008/0114444 A1 | 5/2008 | Yu |
| 2008/0114445 A1 | 5/2008 | Melsheimer et al. |
| 2008/0147173 A1 | 6/2008 | Mciff et al. |
| 2008/0167704 A1* | 7/2008 | Wright ............... A61F 2/07 623/1.12 |
| 2008/0195190 A1 | 8/2008 | Bland et al. |
| 2008/0195191 A1 | 8/2008 | Luo et al. |
| 2008/0215134 A1 | 9/2008 | Lawrence-Brown |
| 2008/0249598 A1 | 10/2008 | Sherry |
| 2008/0262595 A1 | 10/2008 | Chu et al. |
| 2008/0269789 A1 | 10/2008 | Eli |
| 2008/0275540 A1 | 11/2008 | Wen |
| 2008/0275542 A1 | 11/2008 | LaDuca et al. |
| 2008/0288044 A1 | 11/2008 | Osborne |
| 2008/0294234 A1 | 11/2008 | Hartley et al. |
| 2008/0300665 A1 | 12/2008 | Lootz et al. |
| 2008/0312732 A1 | 12/2008 | Hartley et al. |
| 2008/0319528 A1 | 12/2008 | Yribarren et al. |
| 2009/0012597 A1 | 1/2009 | Doig et al. |
| 2009/0012602 A1 | 1/2009 | Quadri |
| 2009/0030497 A1 | 1/2009 | Metcalf et al. |
| 2009/0030502 A1 | 1/2009 | Sun et al. |
| 2009/0048663 A1 | 2/2009 | Greenberg |
| 2009/0054967 A1 | 2/2009 | Das |
| 2009/0062899 A1 | 3/2009 | Dang et al. |
| 2009/0069881 A1 | 3/2009 | Chalekian et al. |
| 2009/0069882 A1 | 3/2009 | Venturelli et al. |
| 2009/0082841 A1 | 3/2009 | Zacharias et al. |
| 2009/0082847 A1 | 3/2009 | Zacharias et al. |
| 2009/0099647 A1 | 4/2009 | Glimsdale et al. |
| 2009/0099648 A1 | 4/2009 | Yu |
| 2009/0099649 A1 | 4/2009 | Chobotov et al. |
| 2009/0099650 A1 | 4/2009 | Bolduc et al. |
| 2009/0105809 A1 | 4/2009 | Lee et al. |
| 2009/0112233 A1 | 4/2009 | Xiao |
| 2009/0125096 A1 | 5/2009 | Chu et al. |
| 2009/0138067 A1 | 5/2009 | Pinchuk et al. |
| 2009/0149877 A1 | 6/2009 | Hanson et al. |
| 2009/0164001 A1 | 6/2009 | Biggs et al. |
| 2009/0171437 A1 | 7/2009 | Brocker et al. |
| 2009/0192587 A1 | 7/2009 | Frid |
| 2009/0227997 A1 | 9/2009 | Wang et al. |
| 2009/0240316 A1* | 9/2009 | Bruszewski ............ A61F 2/07 623/1.13 |
| 2009/0248134 A1 | 10/2009 | Dierking et al. |
| 2009/0254170 A1 | 10/2009 | Hartley et al. |
| 2009/0259290 A1 | 10/2009 | Bruszewski et al. |
| 2009/0287145 A1 | 11/2009 | Cragg et al. |
| 2010/0004728 A1 | 1/2010 | Rao et al. |
| 2010/0029608 A1 | 2/2010 | Finley et al. |
| 2010/0057186 A1 | 3/2010 | West et al. |
| 2010/0063575 A1 | 3/2010 | Shalev et al. |
| 2010/0070019 A1 | 3/2010 | Shalev |
| 2010/0082091 A1 | 4/2010 | Berez et al. |
| 2010/0161026 A1 | 6/2010 | Brocker et al. |
| 2010/0211159 A1 | 8/2010 | Schmid et al. |
| 2010/0249899 A1 | 9/2010 | Chuter et al. |
| 2010/0256725 A1 | 10/2010 | Rasmussen |
| 2010/0274187 A1 | 10/2010 | Argentine |
| 2010/0292774 A1 | 11/2010 | Shalev |
| 2010/0318171 A1 | 12/2010 | Porter et al. |
| 2011/0022149 A1 | 1/2011 | Cox et al. |
| 2011/0022153 A1 | 1/2011 | Schreck et al. |
| 2011/0093002 A1 | 4/2011 | Rucker et al. |
| 2011/0125251 A1 | 5/2011 | Cottone et al. |
| 2011/0208289 A1* | 8/2011 | Shalev ................ A61F 2/07 623/1.15 |
| 2011/0208296 A1 | 8/2011 | Duffy et al. |
| 2011/0208297 A1 | 8/2011 | Tuval et al. |
| 2011/0208298 A1 | 8/2011 | Tuval et al. |
| 2011/0218607 A1 | 9/2011 | Arbefeuille et al. |
| 2011/0218609 A1 | 9/2011 | Chobotov et al. |
| 2011/0257720 A1 | 10/2011 | Peterson et al. |
| 2011/0264184 A1* | 10/2011 | Heltai .................. A61F 2/06 623/1.1 |
| 2011/0264192 A1* | 10/2011 | Hartley ............... A61F 2/07 623/1.13 |
| 2011/0270385 A1* | 11/2011 | Muzslay ............. A61F 2/07 623/1.35 |
| 2011/0288622 A1 | 11/2011 | Chan et al. |
| 2011/0301702 A1 | 12/2011 | Rust et al. |
| 2011/0319983 A1 | 12/2011 | Zhu et al. |
| 2012/0150274 A1 | 6/2012 | Shalev et al. |
| 2012/0172929 A1 | 7/2012 | Shalev |
| 2012/0172965 A1* | 7/2012 | Kratzberg ........... A61F 2/962 623/1.12 |
| 2012/0179236 A1 | 7/2012 | Benary et al. |
| 2012/0185031 A1 | 7/2012 | Ryan et al. |
| 2012/0271401 A1 | 10/2012 | Bruszewski et al. |
| 2012/0310324 A1 | 12/2012 | Benary et al. |
| 2012/0316634 A1 | 12/2012 | Shalev et al. |
| 2012/0323305 A1 | 12/2012 | Benary et al. |
| 2012/0330399 A1 | 12/2012 | Shalev et al. |
| 2013/0013050 A1 | 1/2013 | Shalev et al. |
| 2013/0013051 A1 | 1/2013 | Benary |
| 2013/0035751 A1 | 2/2013 | Shalev |
| 2013/0090722 A1 | 4/2013 | Shalev et al. |
| 2013/0116773 A1* | 5/2013 | Roeder ................ A61F 2/07 623/1.15 |
| 2013/0131783 A1 | 5/2013 | Shalev et al. |
| 2013/0197454 A1 | 8/2013 | Shibata et al. |
| 2013/0204311 A1 | 8/2013 | Kunis |
| 2013/0204343 A1 | 8/2013 | Shalev |
| 2013/0261994 A1 | 10/2013 | Raz et al. |
| 2013/0274866 A1 | 10/2013 | Cox et al. |
| 2013/0289587 A1 | 10/2013 | Shalev |
| 2013/0297005 A1 | 11/2013 | Shalev |
| 2013/0338753 A1 | 12/2013 | Geusen |
| 2014/0052236 A1 | 2/2014 | Shalev |
| 2014/0148888 A1* | 5/2014 | Barrand ............... A61F 2/856 623/1.2 |
| 2014/0172072 A1 | 6/2014 | Shalev |
| 2014/0180378 A1* | 6/2014 | Roeder ................ A61F 2/95 623/1.11 |
| 2014/0288635 A1 | 9/2014 | Shalev |
| 2014/0316510 A1 | 10/2014 | Berra |
| 2014/0324154 A1 | 10/2014 | Shalev |
| 2014/0350658 A1* | 11/2014 | Benary ................ A61F 2/07 623/1.15 |
| 2015/0196301 A1* | 7/2015 | Bodewadt ............ A61F 2/01 606/200 |
| 2015/0374383 A1* | 12/2015 | Bodewadt ............ A61F 2/82 606/157 |
| 2016/0262880 A1* | 9/2016 | Li ........................ A61F 2/2418 |

FOREIGN PATENT DOCUMENTS

| | | |
|---|---|---|
| CN | 2817770 | 9/2006 |
| CN | 201058061 | 5/2008 |
| EP | 1 177 779 A2 | 2/2002 |
| EP | 1177780 | 2/2002 |
| EP | 1325716 | 7/2003 |
| EP | 1470797 | 10/2004 |
| EP | 1759666 | 3/2007 |
| EP | 1961401 | 8/2008 |
| EP | 2266509 | 12/2010 |
| EP | 2298248 | 3/2011 |
| JP | 2002253682 | 9/2002 |
| WO | 96/39104 A1 | 12/1996 |
| WO | 98/06355 | 2/1998 |
| WO | 99/25273 A1 | 5/1999 |
| WO | 9934748 | 7/1999 |
| WO | 99/51165 A1 | 10/1999 |
| WO | 02083038 | 10/2002 |
| WO | 03/034948 A1 | 5/2003 |
| WO | 03099108 | 12/2003 |
| WO | 2004017868 | 3/2004 |
| WO | 2004/045463 A2 | 6/2004 |
| WO | 2005002466 | 1/2005 |
| WO | 2005037138 | 4/2005 |
| WO | 2005041781 | 5/2005 |
| WO | 2005041783 | 5/2005 |
| WO | 2005046524 | 5/2005 |

(56) References Cited

FOREIGN PATENT DOCUMENTS

| WO | 2006007389 | | 1/2006 |
|---|---|---|---|
| WO | 2006028925 | | 3/2006 |
| WO | 2006070372 | | 7/2006 |
| WO | 2006/088905 | A1 | 8/2006 |
| WO | 2006/130755 | A2 | 12/2006 |
| WO | 2007022495 | | 2/2007 |
| WO | 2007039587 | | 4/2007 |
| WO | 2007084547 | | 7/2007 |
| WO | 2007144782 | | 12/2007 |
| WO | 2008008291 | | 1/2008 |
| WO | 2008035337 | | 3/2008 |
| WO | 2008042266 | | 4/2008 |
| WO | 2008047092 | | 4/2008 |
| WO | 2008047354 | | 4/2008 |
| WO | 2008/051704 | A1 | 5/2008 |
| WO | 2008053469 | | 5/2008 |
| WO | 2008066923 | | 6/2008 |
| WO | 2008107885 | | 9/2008 |
| WO | 2008140796 | | 11/2008 |
| WO | 2009078010 | | 6/2009 |
| WO | 2009116041 | | 9/2009 |
| WO | 2009116042 | | 9/2009 |
| WO | 2009118733 | | 10/2009 |
| WO | 2010024869 | | 3/2010 |
| WO | 2010024879 | | 3/2010 |
| WO | 2010027704 | | 3/2010 |
| WO | 2010031060 | | 3/2010 |
| WO | 2010045238 | | 4/2010 |
| WO | 2010062355 | | 6/2010 |
| WO | 2010088776 | | 8/2010 |
| WO | 2010128162 | | 11/2010 |
| WO | 2010150208 | | 12/2010 |
| WO | 2011004374 | | 1/2011 |
| WO | 2011007354 | | 1/2011 |
| WO | 2011055364 | | 5/2011 |
| WO | 2011064782 | | 6/2011 |
| WO | 2011067764 | | 6/2011 |
| WO | 2011070576 | | 6/2011 |
| WO | 2011080738 | | 7/2011 |
| WO | 2011095979 | | 8/2011 |
| WO | 2011106532 | | 9/2011 |
| WO | 2011106533 | | 9/2011 |
| WO | 2011106544 | | 9/2011 |
| WO | 2012/039748 | A2 | 3/2012 |
| WO | 2012049679 | | 4/2012 |
| WO | 2012104842 | | 8/2012 |
| WO | 2012111006 | | 8/2012 |
| WO | 2012117395 | | 9/2012 |
| WO | 2012176187 | | 12/2012 |
| WO | 2013005207 | | 1/2013 |
| WO | 2013030818 | | 3/2013 |
| WO | 2013030819 | | 3/2013 |
| WO | 2013065040 | | 5/2013 |
| WO | 2013084235 | | 6/2013 |
| WO | 2013171730 | | 11/2013 |
| WO | 2014020609 | | 2/2014 |
| WO | 2014108895 | | 7/2014 |
| WO | 2014141232 | | 9/2014 |
| WO | 2014188412 | | 11/2014 |

OTHER PUBLICATIONS

Non-final office action issued in U.S. Appl. No. 14/241,793, dated Feb. 1, 2016.
Non-final office action issued in U.S. Appl. No. 13/807,880, dated Feb. 19, 2016.
A non-final Office Action issued on Feb. 28, 2014 in U.S. Appl. No. 13/512,778.
An International Preliminary Report on Patentability dated Jan. 7, 2014, which issued during the prosecution of Applicant's PCT/IL2012/000269.
An International Preliminary Report on Patentability dated Jan. 4, 2012, which issued during the prosecution of Applicant's PCT/IB2010/052861.
An International Preliminary Report on Patentability dated Dec. 23, 2013, which issued during the prosecution of Applicant's PCT/IL2012/000241.
An International Preliminary Report on Patentability dated Aug. 6, 2013, which issued during the prosecution of Applicant's PCT/IL2012/000060.
An English translation of an Office Action dated Oct. 8, 2014, which issued during the prosecution of Chinese Patent Application No. 201080036970.7.
An English translation of an Office Action dated Nov. 28, 2013, which issued during the prosecution of Chinese Patent Application No. 200880126889.0.
An English translation of an Office Action dated Jan. 28, 2014, which issued during the prosecution of Chinese Patent Application No. 201080036970.7.
An English translation of an Office Action dated May 16, 2014, which issued during the prosecution of Chinese Patent Application No. 200880126889.0.
An English translation of an Office Action dated Aug. 25, 2011, which issued during the prosecution of Chinese Patent Application No. 200880014919.9.
An English translation of an Office Action dated Feb. 16, 2013, which issued during the prosecution of Chinese Patent Application No. 200880126889.0.
An International Preliminary Report on Patentability dated Jan. 10, 2012, which issued during the prosecution of Applicant's PCT/IL2010/000549.
An International Preliminary Report on Patentability dated Jan. 17, 2012, which issued during the prosecution of Applicant's PCT/IL2010/000564.
A Notice of Allowance dated Aug. 2, 2012, which issued during the prosecution of U.S. Appl. No. 12/529,936.
An Advisory Action dated Feb. 13, 2014, which issued during the prosecution of Applicant's U.S. Appl. No. 13/807,880.
An International Preliminary Report on Patentability dated Jun. 5, 2012, which issued during the prosecution of Applicant's PCT/IL2010/000999.
An International Preliminary Report on Patentability dated Jun. 5, 2012, which issued during the prosecution of Applicant's PCT/IL2010/001018.
An International Preliminary Report on Patentability dated Jun. 10, 2014, which issued during the prosecution of Applicant's PCT/IL2012/050506.
A Notice of Allowance issued in U.S. Appl. No. 13/807,906 on Oct. 10, 2014.
A Restriction Requirement dated Jan. 29, 2014, which issued during the prosecution of U.S. Appl. No. 13/519,971.
An International Preliminary Report on Patentability dated Jun. 12, 2012, which issued during the prosecution of Applicant's PCT/IL2010/001037.
An International Preliminary Report on Patentability dated Mar. 4, 2014, which issued during the prosecution of Applicant's PCT/IL2012/000300.
An International Preliminary Report on Patentability dated May 6, 2014, which issued during the prosecution of Applicant's PCT/IL2012/050424.
An International Preliminary Report on Patentability dated May 8, 2012, which issued during the prosecution of Applicant's PCT/IL2010/000917.
An International Preliminary Report on Patentability dated Nov. 18, 2014, which issued during the prosecution of Applicant's PCT/IL2012/000190.
An International Search Report and a Written Opinion both dated Apr. 18, 2011, which issued during the prosecution of Applicant's PCT/IL2010/001037.
An International Search Report and a Written Opinion both dated Aug. 4, 2011, which issued during the prosecution of Applicant's PCT/IL2010/000999.
An International Search Report and a Written Opinion both dated Aug. 31, 2012, which issued during the prosecution of Applicant's PCT/IL2012/000148.

(56) References Cited

OTHER PUBLICATIONS

An International Search Report and a Written Opinion both dated Dec. 3, 2010, which issued during the prosecution of Applicant's PCT/IL2010/000564.
An International Search Report and a Written Opinion both dated Feb. 4, 2011, which issued during the prosecution of Applicant's PCT/IB2010/052861.
An International Search Report and a Written Opinion both dated Jul. 13, 2012, which issued during the prosecution of Applicant's PCT/IL2012/000083.
An International Search Report and a Written Opinion both dated Jul. 17, 2012, which issued during the prosecution of Applicant's PCT/IL2012/000095.
An International Search Report and a Written Opinion both dated Jun. 14, 2013, which issued during the prosecution of Applicant's PCT/IL2012/050506.
An International Search Report and a Written Opinion both dated Jun. 28, 2011, which issued during the prosecution of Applicant's PCT/IL2011/000135.
An International Search Report and a Written Opinion both dated Jun. 30, 2009, which issued during the prosecution of Applicant's PCT/IL2008/001621.
An International Search Report and a Written Opinion both dated Mar. 10, 2011, which issued during the prosecution of Applicant's PCT/IL2010/000917.
An International Search Report and a Written Opinion both dated Mar. 11, 2009, which issued during the prosecution of Applicant's PCT/IL2007/001312.
An International Search Report and a Written Opinion both dated Mar. 15, 2013, which issued during the prosecution of Applicant's PCT/IL2012/050424.
An International Preliminary Report on Patentability dated Sep. 3, 2013, which issued during the prosecution of Applicant's PCT/IL2012/000095.
An International Search Report and a Written Opinion both dated Mar. 30, 2011, which issued during the prosecution of Applicant's PCT/IL2010/001018.
An International Search Report and a Written Opinion both dated May 23, 2011, which issued during the prosecution of Applicant's PCT/IL2010/001087.
An International Search Report and a Written Opinion both dated Nov. 5, 2010, which issued during the prosecution of Applicant's PCT/IL2010/000549.
An International Search Report and a Written Opinion both dated Nov. 27, 2012, which issued during the prosecution of Applicant's PCT/IL2012/000300.
An International Search Report and a Written Opinion both dated Oct. 1, 2012, which issued during the prosecution of Applicant's PCT/IL2012/000241.
An International Search Report and a Written Opinion both dated Oct. 4, 2012, which issued during the prosecution of Applicant's PCT/IL2012/000269.
An International Search Report and a Written Opinion both dated Sep. 6, 2012, which issued during the prosecution of Applicant's PCT/IL2012/000190.
An International Search Report and a Written Opinion both dated Apr. 28, 2014, which issued during the prosecution of Applicant's PCT/IL2014/050019.
An International Search Report dated Jul. 30, 2014, which issued during the prosecution of Applicant's PCT/IL2014/050174.
An International Search Report and a Written Opinion both dated Sep. 24, 2012, which issued during the prosecution of Applicant's PCT/IL2012/000060.
An International Search Report and a Written Opinion both dated Sep. 29, 2008, which issued during the prosecution of Applicant's PCT/IL2008/000287.
An International Search Report and a Written Opinion both dated Nov. 26, 2013, which issued during the prosecution of Applicant's PCT/IL2013/050656.
Notice of allowance dated Jun. 24, 2014, which issued during the prosecution of Applicant's U.S. Appl. No. 13/380,278.
An International Search Report dated Nov. 28, 2014, which issued during the prosecution of Applicant's PCT/IL2014/050434.
An Interview Summary dated Feb. 28, 2012, which issued during the prosecution of U.S. Appl. No. 12/529,936.
An Office Action dated Apr. 10, 2014, which issued during the prosecution of Applicant's U.S. Appl. No. 13/807,906.
An Office Action dated Apr. 24, 2014, which issued during the prosecution of Applicant's U.S. Appl. No. 13/380,278.
An Office Action dated Dec. 2, 2013, which issued during the prosecution of U.S. Appl. No. 13/807,880.
An office Action dated Feb. 25, 2013, which issued during the prosecution of U.S. Appl. No. 13/031,871.
An Office Action dated Feb. 27, 2013, which issued during the prosecution of U.S. Appl. No. 12/808,037.
An Office Action dated Jul. 24, 2014, which issued during the prosecution of Canadian Patent Application No. 2768228.
An Office Action dated Jul. 28, 2014, which issued during the prosecution of U.S. Appl. No. 13/031,871.
An Office Action dated Jun. 19, 2012, which issued during the prosecution of U.S. Appl. No. 12/808,037.
An Office Action dated Mar. 24, 2011, which issued during the prosecution of U.S. Appl. No. 12/529,936.
An Office Action dated Mar. 28, 2014, which issued during the prosecution of Applicant's U.S. Appl. No. 13/519,971.
An Office Action dated Apr. 27, 2011, which issued during the prosecution of U.S. Appl. No. 12/447,684.
An Office Action dated Apr. 28, 2014, which issued during the prosecution of Applicant's U.S. Appl. No. 13/939,798.
An Office Action dated May 20, 2013, which issued during the prosecution of U.S. Appl. No. 13/807,880.
An Office Action dated Nov. 12, 2010, which issued during the prosecution of U.S. Appl. No. 12/447,684.
An Office Action dated Nov. 3, 2014, which issued during the prosecution of Canadian Patent Application No. 2767596.
An Office Action dated Nov. 19, 2013, which issued during the prosecution of U.S. Appl. No. 13/663,117.
An Office Action dated Oct. 11, 2012, which issued during the prosecution of U.S. Appl. No. 13/031,871.
U.S. Appl. No. 61/219,758, filed Jun. 23, 2009.
U.S. Appl. No. 61/221,074, filed Jun. 28, 2009.
U.S. Appl. No. 61/496,613, filed Jun. 14, 2011.
An Office Action dated Oct. 28, 2011, which issued during the prosecution of U.S. Appl. No. 12/529,936.
U.S. Appl. No. 61/505,132, filed Jul. 7, 2011.
U.S. Appl. No. 61/678,182, filed Aug. 1, 2012.
U.S. Appl. No. 61/529,931, filed Sep. 1, 2011.
U.S. Appl. No. 61/553,209, filed Oct. 30, 2011.
U.S. Appl. No. 61/499,195, filed Jun. 21, 2011.
U.S. Appl. No. 61/749,965, filed Jan. 8, 2013.
Notice of Allowance dated Jun. 18, 2013, which issued during the prosecution of U.S. Appl. No. 13/523,296.
Office Action issued on Oct. 27, 2014 in Canadian Patent Application No. 2,785,953.
Ryhanen J., in "Biocompatibility evaluation of nickel-titanium shape memory metal alloy," Academic Dissertation, Faculty of Medicine, Department of Surgery, University of Oulu, Finland (May 1999).
Supplementary European Search Report dated Dec. 13, 2012, which issued during the prosecution of Applicant's European App No. 08719912.1.
Supplementary European Search Report dated Feb. 17, 2014, which issued during the prosecution of Applicant's European App No. 12803376.8.
Supplementary European Search Report dated Jun. 23, 2014, which issued during the prosecution of Applicant's European App No. 12741804.4.
"E-vita® open plus" product brochure (JOTEC GmbH, Hechingen, Germany), 2010.
An Office action dated Sep. 4, 2014, from the U.S. Patent and Trademark Office in counterpart U.S. Appl. No. 13/519,971.

(56) References Cited

OTHER PUBLICATIONS

European Office Action issued Dec. 17, 2014 in European Patent Application No. 12803376.8.
An Office action dated Feb. 5, 2015, from the U.S. Patent and Trademark Office in counterpart U.S. Appl. No. 13/384,075.
European Search Report issued Feb. 24, 2014 in European Patent Application No. 12803376.8.
Fattori et al., Degenerative aneurysm of the descending aorta. Endovascular Treatment. pp. 1-11, 2007, European Association for Cardio-Thoracic Surgery.
International Preliminary Report on Patentability dated Jan. 12, 2010 in corresponding International Application No. PCT/IL2008/000287.
Fonseca A et al., "Intravascular ultrasound assessment of the novel AngioSculpt scoring balloon catheter for the treatment of complex coronary lesions," J Invasive Cardiol 20(1):21-7 (Jan. 2008).
Van Prehn J et al., "Oversizing of aortic stent grafts for abdominal aneurysm repair: a systematic review of the benefits and risks," Eur J Vase Endovase Surg. Jul. 2009;38(I):42-53. Epub May 9, 2009 (abstract only).
Invitation to Pay Additional Fees dated May 13, 2014, which issued during the prosecution of Applicant's PCT/IL2014/050019.
Invitation to Pay Additional Fees dated May 8, 2014, which issued during the prosecution of Applicant's PCT/IL2014/50174.
Khlif H et al., "Contribution to the Improvement of Textile Vascular Prostheses Crimping," Trends in Applied Sciences Research 6(9):1019-1027 (2011).
U.S. Appl. No. 61/775,964, filed Mar. 11, 2013.
U.S. Appl. No. 61/826,544, filed May 23, 2013.
U.S. Appl. No. 61/906,014, filed Nov. 19, 2013.
U.S. Appl. No. 61/926,533, filed Jan. 13, 2014.
U.S. Appl. No. 61/528,242, filed Aug. 28, 2011.
An Office Action dated Aug. 15, 2014, which issued during the prosecution of Applicant's U.S. Appl. No. 13/939,798.
U.S. Appl. No. 61/566,654, filed Dec. 4, 2011.
An English translation of an Office Action dated Mar. 19, 2015, which issued during the prosecution of Chinese Patent Application No. 201080036970.7.
A Notice of Allowance dated Jan. 20, 2015, which issued during the prosecution of U.S. Appl. No. 13/383,128.
A Notice of Allowance dated Nov. 7, 2014, which issued during the prosecution of U.S. Appl. No. 13/512,778.
An Office Action dated Aug. 15, 2014, which issued during the prosecution of U.S. Appl. No. 13/512,778.
An International Search Report and a Written Opinion both dated Mar. 18, 2015, which issued during the prosecution of Applicant's PCT/IL2014/050973.
An Office Action dated Apr. 14, 2015, which issued during the prosecution of U.S. Appl. No. 14/130,213.
An International Preliminary Report on Patentability dated Feb. 3, 2015, which issued during the prosecution of Applicant's PCT/IL2013/050656.
A Notice of Allowance dated Jan. 7, 2014, which issued during the prosecution of U.S. Appl. No. 13/663,117.
An Office Action dated Mar. 26, 2015, which issued during the prosecution of U.S. Appl. No. 13/514,240.
Supplementary European Search Report dated Oct. 31, 2014, which issued during the prosecution of Applicant's European App No. 12752054.2.
An Office Action dated Sep. 2, 2014, which issued during the prosecution of U.S. Appl. No. 12/447,684.
U.S. Appl. No. 61/448,199, filed Mar. 2, 2011.
U.S. Appl. No. 61/014,031, filed Dec. 15, 2007.
An Examiner Interview Summary dated Dec. 13, 2010, which issued during the prosecution of U.S. Appl. No. 12/447,684.
An Office Action dated Mar. 21, 2012, which issued during the prosecution of U.S. Appl. No. 12/808,037.
An Office Action dated May 22, 2013, which issued during the prosecution of U.S. Appl. No. 12/808,037.
U.S. Appl. No. 60/863,373, filed Oct. 29, 2006.
An International Preliminary Report on Patentability dated Aug. 21, 2013, which issued during the prosecution of Applicant's PCT/IL2012/000083.
European Search Report dated Jun. 12, 2015, which issued during the prosecution of Applicant's European App No. 12855964.8.
European Search Report dated Feb. 26, 2015, which issued during the prosecution of Applicant's European App No. 12806964.8.
European Search Report dated Mar. 20, 2015, which issued during the prosecution of Applicant's European App No. 08861980.4.
An Office Action dated Feb. 3, 2015, which issued during the prosecution of U.S. Appl. No. 12/447,684.
An Office Action dated Oct. 2, 2015, which issued during the prosecution of U.S. Appl. No. 13/577,161.
An International Search Report and a Written Opinion both dated Jul. 30, 2014, which issued during the prosecution of Applicant's PCT/IL2014/050174.
A Non-Final Office Action in U.S. Appl. No. 14/240,600, dated Mar. 7, 2016.
An Extended European Search Report in Application No. 13825456.0, dated Mar. 15, 2016.
Invitation to Pay Additional Fees issued in PCT/IL2016/050014, dated Apr. 12, 2016.
An International Search Report and Written Opinion issued in PCT/IL2016/050049, dated Apr. 22, 2016.
A European Search Report issued in Application No. 10832752.9, dated May 23, 2016.

* cited by examiner

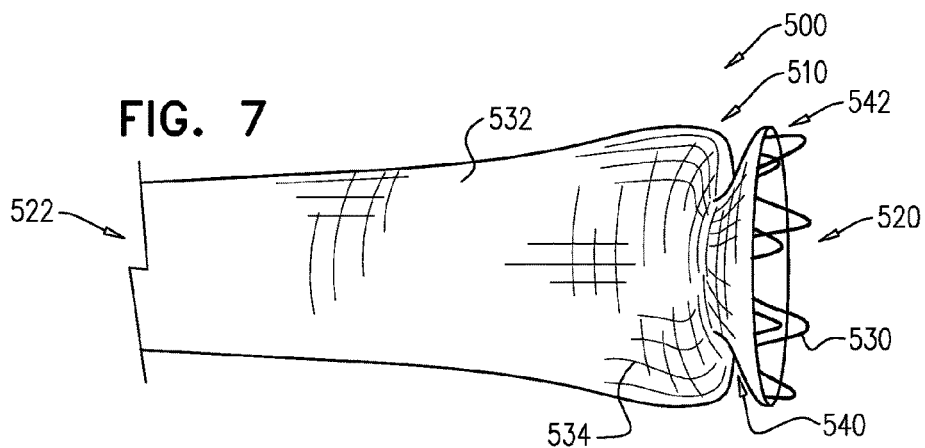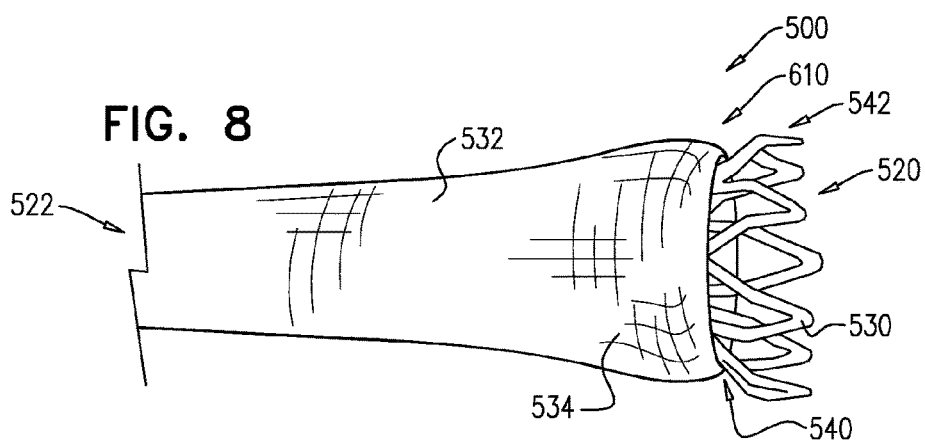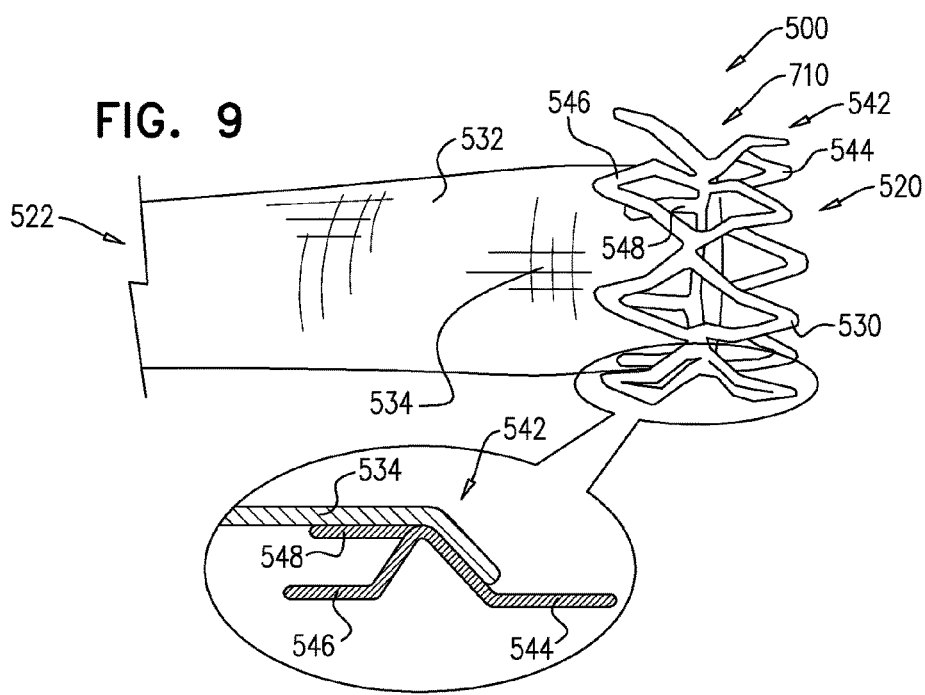

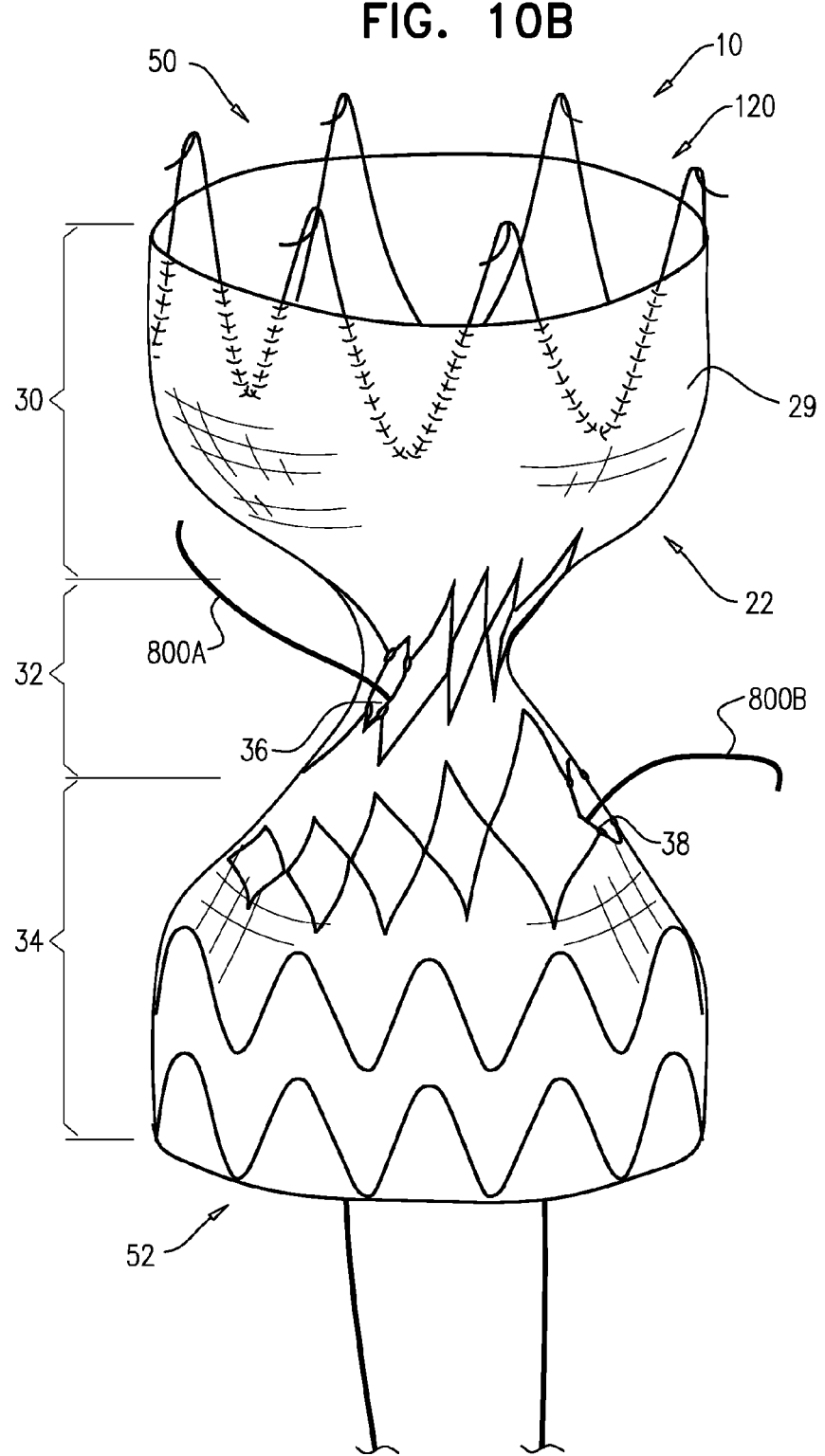

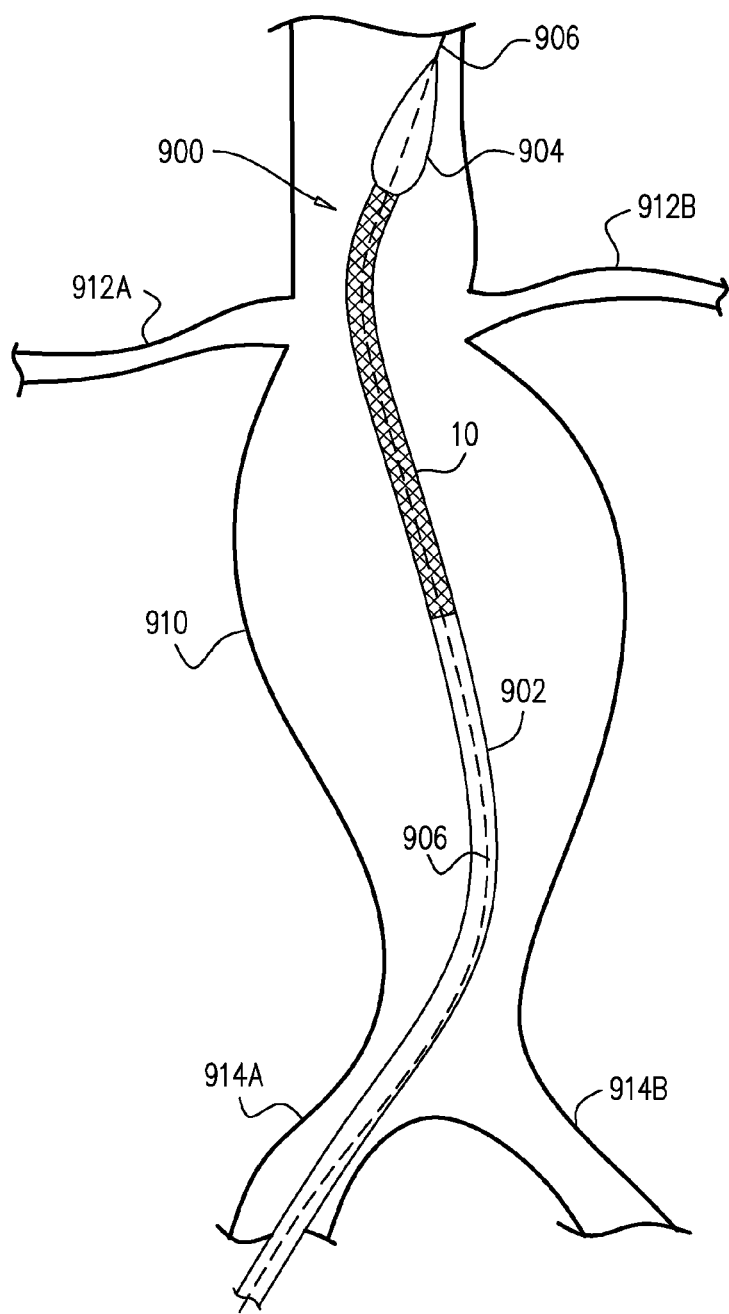

BRANCHED STENT-GRAFT SYSTEM

CROSS-REFERENCE TO RELATED APPLICATIONS

The present application is the U.S. national stage of International Application PCT/IL2012/050506, filed Dec. 4, 2012, which claims priority from U.S. Provisional Application 61/566,654, filed Dec. 4, 2011, which is assigned to the assignee of the present application and is incorporated herein by reference.

FIELD OF THE APPLICATION

This present application relates generally to prostheses and surgical methods, and specifically to tubular prostheses, including endovascular stent-grafts, and surgical techniques for using the prostheses to maintain patency of body passages such as blood vessels, and treating aneurysms.

BACKGROUND OF THE APPLICATION

Endovascular prostheses are sometimes used to treat aortic aneurysms. Such treatment includes implanting a stent or stent-graft within the diseased vessel to bypass the anomaly. An aneurysm is a sac formed by the dilation of the wall of the artery. Aneurysms may be congenital, but are usually caused by disease or, occasionally, by trauma. Aortic aneurysms which commonly form between the renal arteries and the iliac arteries are referred to as abdominal aortic aneurysms ("AAAs"). Other aneurysms occur in the aorta, such as thoracic aortic aneurysms ("TAAs"), which may occur in one or more of the descending aorta, the ascending aorta, and the aortic arch.

Stent-grafts sometimes are implanted in patients having aneurysms close to or crossing branch openings to renal arteries or other branch arteries (e.g., the celiac artery, suprarenal artery, or superior or interior mesenteric arteries). Such stent-grafts have lateral openings avoid impairing blood flow from the aorta to these branching arteries from the aorta.

SUMMARY OF APPLICATIONS

Some applications of the present invention provide a main endovascular stent-graft, which comprises a generally tubular hourglass-shaped body, which is shaped so as to define a narrow waist portion longitudinally surrounded and adjacent to wider first and second longitudinal portions. Fabric of a fluid flow guide of the stent-graft along the waist portion is shaped so as to define at least first and second lateral apertures. The lateral apertures are configured for coupling to branching stent-grafts.

The axial and circumferential locations of the ostia of arteries that branch from the aorta vary substantially from patient to patient. Among these arteries, those that may not be occluded by an aortic stent-graft include the left and right renal arteries, the celiac artery, and the superior mesenteric artery (SMA). The hourglass shape of the main stent-graft enables the main stent-graft to accommodate this varying anatomy, without requiring customization of the main stent-graft for each patient to align the lateral apertures with the patient's ostia. Branching stent-grafts are coupled to the lateral apertures after the main stent-graft has been deployed in the aorta. The hourglass shape provides space between the lateral apertures and the ostia, in which space the surgeon can manipulate the branching stent-grafts in order to accommodate any axial or circumferential misalignment between the lateral apertures and the ostia. Typically, the hourglass shape enables the main stent-graft to accommodate up to about 1 cm in axial misalignment between the lateral apertures and the respective ostia of the branching vessels.

Each of the branching stent-grafts is shaped so as to define an interface portion near a first end thereof. When the branching stent-graft is in the radially-expanded deployment configuration, the interface portion is shaped so as to define a stricture, i.e., a narrow portion, on either longitudinal side of which the branching stent-graft is wider. The stricture is sized and shaped to be placed within, and securely interface with, one of the first and second lateral apertures of the main stent-graft, so as to form a blood-tight seal with the perimeter of the lateral aperture. Each of the branching stent-grafts comprises structural stent elements that help define the stricture, and thus provide a solid structural interface with the lateral aperture, as well as some tolerance to deployment positioning errors by the operators, as the slopes on each side of the stricture tend to centralize the narrowest portion of the stricture at a plane similar to that of the lateral apertures. When the branching stent-graft is in the radially-expanded deployment configuration, a portion of the structural stent elements of the interface portion extends beyond the stricture toward the first end of the branching stent-graft, and radially outward, in order to provide good coupling of the interface portion with one of the first and second lateral apertures of the main stent-graft.

When coupled to one of the lateral apertures, the interface portion typically extends radially inward into the lumen of the main stent-graft only slightly, such as by no more than 5 mm, e.g., between 2 and 5 mm, such that the interface portion does not substantially interfere with blood flow through the lumen. Such non-interference with blood flow allows the main stent-graft to have the narrower waist portion, and yet still provide sufficient blood flow through the lumen of this narrower portion, which would not be possible if the interface portions of two or three branching stent-grafts extended too far into the lumen of the main stent-graft.

There is therefore provided, in accordance with an application of the present invention, apparatus including an endovascular stent-graft, which includes a generally tubular hourglass-shaped body, which body (a) is configured to assume a radially-compressed delivery configuration and a radially-expanded deployment configuration, and (b) includes:

a flexible stent member, which includes a plurality of structural stent elements; and a tubular fluid flow guide, which includes a fabric, and is attached to the structural stent elements, wherein the hourglass-shaped body is shaped so as to define a narrow waist portion longitudinally surrounded by and adjacent to wider first and second longitudinal portions, and wherein the fabric along the waist portion is shaped so as to define at least first and second lateral apertures.

For some applications, the first and the second lateral apertures are disposed such that an arc angle around a central longitudinal axis of the body between respective centers of the first and the second lateral apertures is between 120 and 180 degrees when the body is in the radially-expanded deployment configuration.

For some applications, the narrow waist portion, first longitudinal portion, and second longitudinal portion, when the hourglass-shaped body is in the radially-expanded deployment configuration, have waist, first, and second average diameters, respectively, which waist average diameter equals between 60% and 90% of the lesser of the first and the second average diameters.

For some applications, when the hourglass-shaped body is in the radially-expanded deployment configuration, a smallest diameter of the waist portion is no more than 90% of the lesser of (a) a greatest diameter of the first longitudinal portion and (b) a greatest diameter of the second longitudinal portion.

For some applications, when the hourglass-shaped body is in the radially-expanded deployment configuration:
the narrow waist portion has coronal and sagittal waist diameters, and an average waist diameter thereof,
the first longitudinal portion has coronal and sagittal first diameters, and an average first diameter thereof,
the second longitudinal portion has coronal and sagittal second diameters, and an average second diameter thereof,
wherein the average waist diameter equals between 60% and 90% of the lesser of the average first diameter and the average second diameter.

For some applications, the narrow waist portion, first longitudinal portion, and second longitudinal portion, when the hourglass-shaped body is in the radially-expanded deployment configuration, have waist, first, and second average perimeters, respectively, which waist average perimeter equals between 60% and 90% of the lesser of the first and the second average perimeters.

For some applications, when the hourglass-shaped body is in the radially-expanded deployment configuration, a smallest perimeter of the waist portion is no more than 90% of the lesser of (a) a greatest perimeter of the first longitudinal portion and (b) a greatest perimeter of the second longitudinal portion.

For some applications, one or more of the structural stent elements are attached to the fabric along at least a portion of the waist portion, and are shaped so as to define the first and the second lateral apertures, respectively, when the hourglass-shaped body is in the radially-expanded deployment configuration.

For some applications, the waist portion, first longitudinal portion, and the second longitudinal portion have respective longitudinal lengths, each of which lengths is at least 10 mm.

For some applications, one or more first ones of the structural stent elements are attached to the fabric along at least a portion of the first longitudinal portion, one or more second ones of the structural stent elements are attached to the fabric along at least a portion of the waist portion, and one or more third ones of the structural stent elements are attached to the fabric along at least a portion of the second longitudinal portion. For some applications, none of the one or more first structural stent elements is in direct contact with any of the one or more second structural stent elements when the hourglass-shaped body is in the radially-expanded deployment configuration. Alternatively or additionally, for some applications, none of the one or more third structural stent elements is in direct contact with any of the one or more second structural stent elements when the hourglass-shaped body is in the radially-expanded deployment configuration.

For some applications, an axial distance between the respective centers of the first and the second lateral apertures, measured along the central longitudinal axis of the hourglass-shaped body, is no more than 2 cm.

For some applications, fabric along the first portion is shaped so as to define a superior aperture. For some applications, the superior aperture is disposed so as to define a superior aperture arc angle around the central longitudinal axis between (a) a center of the superior aperture and (b) a midpoint of an arc angle between respective centers of the first and the second lateral apertures, the superior aperture arc angle being less than 60 degrees when the hourglass-shaped body is in the radially-expanded deployment configuration. For some applications, a perimeter of the superior aperture is between 18 and 35 mm.

For some applications, the structural stent elements include first and second structural stent elements, which are attached to the fabric along at least a portion of the waist portion, and are shaped so as to define the first and the second lateral apertures, respectively, when the hourglass-shaped body is in the radially-expanded deployment configuration. For some applications, the first and the second structural stent elements do not circumferentially overlap when the hourglass-shaped body is in the radially-expanded deployment configuration. For some applications, the first and second structural stent elements are shaped so as define respective closed-cell orifices characterized by respective centers, and the centers generally coincide with the centers of the first and the second lateral apertures, respectively, when the hourglass-shaped body is in the radially-expanded deployment configuration. For some applications, each of the first and the second structural stent elements circumscribes an arc angle of between 50 and 170 degrees, when the hourglass-shaped body is in the radially-expanded deployment configuration. For some applications, the first and the second structural stent elements are not in direct contact with each other when the hourglass-shaped body is in the radially-expanded deployment configuration. For some applications, the first and the second structural stent elements are axially separated therebetween when the hourglass-shaped body is in the radially-expanded deployment configuration. For some applications, the first and the second structural stent elements circumferentially and/or axially overlap when the hourglass-shaped body is in the radially-expanded deployment configuration.

For some applications, the first structural stent element is shaped substantially as an axial inversion of the second structural stent element when the hourglass-shaped body is in the radially-expanded deployment configuration. For some applications, the first and the second structural stent elements are shaped so as to define respective trapezoids when the hourglass-shaped body is in the radially-expanded deployment configuration. For example, the trapezoids may be right trapezoids. For some applications, the first and the second structural stent elements are shaped so as to define right triangles when the hourglass-shaped body is in the radially-expanded deployment configuration.

For some applications, the apparatus further includes at least first and second generally tubular branching stent-grafts, which are shaped so as to define respective interface portions that are configured to be coupled to the first and the second lateral apertures, respectively. For some applications, the first and the second branching stent grafts are self-expandable from respective branching radially-compressed delivery configurations to respective branching radially-expanded deployment configurations.

For some applications, the first branching stent-graft includes:
a flexible branching stent member, which includes a plurality of branching structural stent elements; and
a tubular branching fluid flow guide, which includes a branching fabric, and is attached to the branching structural stent elements,
wherein, when the first branching stent-graft is in the branching radial-expanded deployment configuration, the branching structural stent elements are shaped so as to define a stricture near a first end of the first branching stent-graft, which stricture is sized to be securely coupled to the first lateral aperture of the main stent-graft.

For some applications, the stricture is positioned within 5 mm of the first end of the first branching stent-graft. For some applications, the branching fabric covers, and is securely attached to, the branching structural stent elements that extend beyond the stricture toward an end of the first branching stent-graft that is coupled to the first lateral aperture, when the first branching stent-graft is in the branching radial-expanded deployment configuration. For some applications, one or more of the branching structural stent elements define the stricture. For some applications, a diameter of the branching structural stent elements adjacently distal the stricture is at least 5% greater than a diameter of the branching fabric at the same longitudinal location along the branching stent graft, when the first branching stent-graft is in the branching radially-expanded deployment configuration.

For some applications, the interface portion of the first branching stent-graft is at a first end of the first stent-graft, and a diameter of the first branching stent graft generally monotonously does not decrease from a second end of the first stent-graft to the first end of the first stent-graft. For some applications, the diameter of the first branching stent-graft at the first end thereof is at least 20% greater than the diameter of the first branching stent-graft at the second end thereof.

For some applications, the apparatus further includes an endovascular angioplasty balloon including a proximal lobe and a distal lobe and a radiopaque marker positioned therebetween, and the proximal and distal lobes of the balloon are sized to be expandable to at least 10% greater than a greater of (a) a diameter the first lateral aperture and (b) a diameter of the second lateral aperture.

For some applications, the apparatus further includes at least another stent-graft, and the main stent-graft and the other stent-graft are longitudinally coupled together to so as to form a substantially blood impervious seal. For some applications, the second longitudinal portion of the main stent-graft is positioned inside the other stent-graft. Alternatively, the other stent-graft is positioned inside the second longitudinal portion of the main stent-graft. For some applications, the other stent-graft includes an additional endovascular system shaped so as to define one blood entry lumen and at least two blood exit lumens, and the blood entry lumen is coupled with the second longitudinal portion of main stent-graft.

For some applications, the waist portion is configured to assume an intermediate deployment configuration, in which configuration the second average diameter is at least 10% less than when the hourglass-shaped body is in the radially-expanded deployment configuration. For some applications, the apparatus further includes a releasable latching mechanism, which is configured to assume a latched state in which the mechanism confines the structural stent elements of the waist portion in the intermediate deployment configuration. For some applications, the releasable latching mechanism is configured to effect a transition of the waist portion from the intermediate deployment configuration to the radially-expanded deployment configuration upon a triggering event. For some applications, the triggering event is an exertion of outward radial pressure inside the waist portion. For some applications, the releasable latching mechanism includes a longitudinal latching shaft that passes along at least a portion of the central longitudinal axis, and the triggering event is a generally axial translation of the longitudinal latching shaft. For some applications, the releasable latching mechanism includes a longitudinal latching shaft that passes along at least a portion of the central longitudinal axis, and the triggering event is a generally rotational translation of the longitudinal latching shaft.

For some applications, the fabric along the first longitudinal portion is shaped so as to define at least one superior scallop, the superior scallop being characterized by a width and a height, when the hourglass-shaped body is in the radially-expanded deployment configuration. For some applications, the superior scallop is disposed so as to define a superior scallop arc angle around the central longitudinal axis between (a) a center of the superior scallop and (b) a midpoint of an arc angle between respective centers of the first and the second lateral apertures, the superior scallop arc angle being less than 60 degrees when the hourglass-shaped body is in the radially-expanded deployment configuration. For some applications, the width of superior scallop is between 5 and 12 mm. Alternatively or additionally, for some applications, the height of superior scallop is between 5 and 25 mm.

For some applications, the hourglass-shaped body has an elliptical cross-section perpendicular to the central longitudinal axis of the hourglass-shaped body, when the hourglass-shaped body is in the radially-expanded deployment configuration. For some applications, the elliptical cross-section is circular when the hourglass-shaped body is in the radially-expanded deployment configuration.

For some applications, the second portion is shaped so as to define a constant diameter cylinder when the hourglass-shaped body is in the radially-expanded deployment configuration.

For some applications, the second portion is shaped so as to define a radially concave tube when the hourglass-shaped body is in the radially-expanded deployment configuration.

For some applications, the second portion is shaped so as to define an inward trapezoid when the hourglass-shaped body is in the radially-expanded deployment configuration.

For some applications, the first average diameter is between 25 and 40 mm.

For some applications, the second average diameter is between 20 and 35 mm.

For some applications, the waist diameter is between 15 and 30 mm.

For some applications, a diameter of each of the lateral apertures is between 6 and 15 mm.

For some applications, a ratio between an average diameter of the second longitudinal portion and a diameter of each of the lateral apertures is between 1.3 and 6.

For some applications, a ratio between an average diameter of the first longitudinal portion and a diameter of each of the lateral apertures is between 1.5 and 7.

For some applications, a ratio between an average diameter of the waist portion and a diameter of each of the lateral apertures is between 1 and 5.

For some applications, the structural stent elements include a metal. For some applications, the metal includes a superelastic alloy. For some applications, the metal includes a shape memory alloy.

There is further provided, in accordance with an application of the present invention, apparatus including an endovascular stent-graft, which includes a generally tubular body, which body (a) is configured to assume a radially-compressed delivery configuration and a radially-expanded deployment configuration, and (b) includes:

a flexible stent member, which includes a plurality of structural stent elements, which include:
one or more first structural stent elements that include one or more respective radiopaque wires; and
one or more second structural stent elements that are less radiopaque than the radiopaque wires; and
a tubular fluid flow guide, which includes a fabric, and is attached to the structural stent elements,
wherein the fabric and the one or more radiopaque wires are shaped so as to together define one or more lateral apertures through the body.

For some applications, the second structural stent elements include a metal selected from the group consisting of: Nitinol, stainless steel, and cobalt chromium. Alternatively or additionally, for some applications, the one or more radiopaque wires include a metal selected from the group consisting of: tungsten, gold, titanium, and iridium.

For some applications, a collective mass of the second structural stent elements equals at least 10 times a collective mass of the one or more radiopaque wires.

There is still further provided, in accordance with an application of the present invention, a method including:
providing an endovascular stent-graft, which includes a generally tubular hourglass-shaped body, which includes (a) a flexible stent member, which includes a plurality of structural stent elements, and (b) a tubular fluid flow guide, which includes a fabric, and is attached to the structural stent elements;
transvascularly introducing the stent-graft into a blood vessel of a human subject while the body is in a radially-compressed delivery configuration; and
thereafter, transitioning the body to a radially-expanded deployment configuration in the blood vessel, in which configuration the hourglass-shaped body is shaped so as to define a narrow waist portion longitudinally surrounded by and adjacent to wider first and second longitudinal portions, and the fabric along the second portion is shaped so as to define at least first and second lateral apertures.

For some applications, the method further includes, after transitioning the body to the radially-expanded deployment configuration, transvascularly introducing at least first and second generally tubular branching stent-grafts into vasculature of the subject, and coupling interface portions of the first and second branching stent-grafts to the first and the second lateral apertures, respectively.

For some applications, coupling the interface portion of the first branching stent-graft to the first lateral aperture includes coupling the interface portion of the first branching stent-graft to the first lateral aperture such that the interface portion extends radially inward into a lumen of the main stent-graft by no more than 5 mm.

For some applications, transvascularly introducing the first branching stent-graft includes:
introducing a guidewire through one end of the main stent-graft, out of the first lateral aperture, and into a branching blood vessel that branches from the blood vessel, while the first branching stent-graft is in a radially-compressed delivery configuration; and
introducing the first branching stent-graft over the guidewire, through the first lateral aperture, and into the branching blood vessel.

For some applications, the first and the second lateral apertures are disposed such that an arc angle around a central longitudinal axis of the body between respective centers of the first and the second lateral apertures is between 120 and 180 degrees when the body is in the radially-expanded deployment configuration.

For some applications, the narrow waist portion, first longitudinal portion, and second longitudinal portion, when the hourglass-shaped body is in the radially-expanded deployment configuration, have waist, first, and second average diameters, respectively, which waist average diameter equals between 60% and 90% of the lesser of the first and the second average diameters.

For some applications, when the hourglass-shaped body is in the radially-expanded deployment configuration, a smallest diameter of the waist portion is no more than 90% of the lesser of (a) a greatest diameter of the first longitudinal portion and (b) a greatest diameter of the second longitudinal portion.

For some applications, when the hourglass-shaped body is in the radially-expanded deployment configuration:
the narrow waist portion has coronal and sagittal waist diameters, and an average waist diameter thereof,
the first longitudinal portion has coronal and sagittal first diameters, and an average first diameter thereof,
the second longitudinal portion has coronal and sagittal second diameters, and an average second diameter thereof,
wherein the average waist diameter equals between 60% and 90% of the lesser of the average first diameter and the average second diameter.

For some applications, one or more of the structural stent elements are attached to the fabric along at least a portion of the waist portion, and are shaped so as to define the first and the second lateral apertures, respectively, when the hourglass-shaped body is in the radially-expanded deployment configuration.

There is additionally provided, in accordance with an application of the present invention, a method including:
providing an endovascular stent-graft, which includes a generally tubular body, which includes (a) a flexible stent member, which includes a plurality of structural stent elements, which include (i) one or more first structural stent elements that include one or more respective radiopaque wires, and (ii) one or more second structural stent elements that are less radiopaque than the radiopaque wires, and (b) a tubular fluid flow guide, which includes a fabric, and is attached to the structural stent elements;
transvascularly introducing the stent-graft into a blood vessel of a human subject while the body is in a radially-compressed delivery configuration; and
thereafter, transitioning the body to a radially-expanded deployment configuration in the blood vessel, in which configuration the fabric and the one or more radiopaque wires are shaped so as to together define one or more lateral apertures through the body.

For some applications, the second structural stent elements include a metal selected from the group consisting of: Nitinol, stainless steel, and cobalt chromium. Alternatively or additionally, for some applications, the one or more radiopaque wires include a metal selected from the group consisting of: tungsten, gold, titanium, and iridium.

For some applications, a collective mass of the second structural stent elements equals at least 10 times a collective mass of the one or more radiopaque wires.

The present invention will be more fully understood from the following detailed description of applications thereof, taken together with the drawings, in which:

BRIEF DESCRIPTION OF THE DRAWINGS

FIG. 7 is a schematic illustration of a branching stent-graft, in accordance with an application of the present invention;

FIG. 8 is a schematic illustration of another branching stent-graft, in accordance with an application of the present invention;

FIG. 9 is a schematic illustration of yet another branching stent-graft, in accordance with an application of the present invention;

FIGS. 10A-C are schematic illustrations of a technique for deploying a main stent-graft and branching stent-grafts, in accordance with an application of the present invention;

FIGS. 11A-F are schematic illustrations of an exemplary method of deploying a main stent-graft and two branching stent-grafts in the vicinity of a sub-renal abdominal aortic aneurysm of an abdominal aorta, in accordance with an application of the present invention.

DETAILED DESCRIPTION OF APPLICATIONS

Some applications of the present invention provide a main endovascular stent-graft 10.

Figure 1:
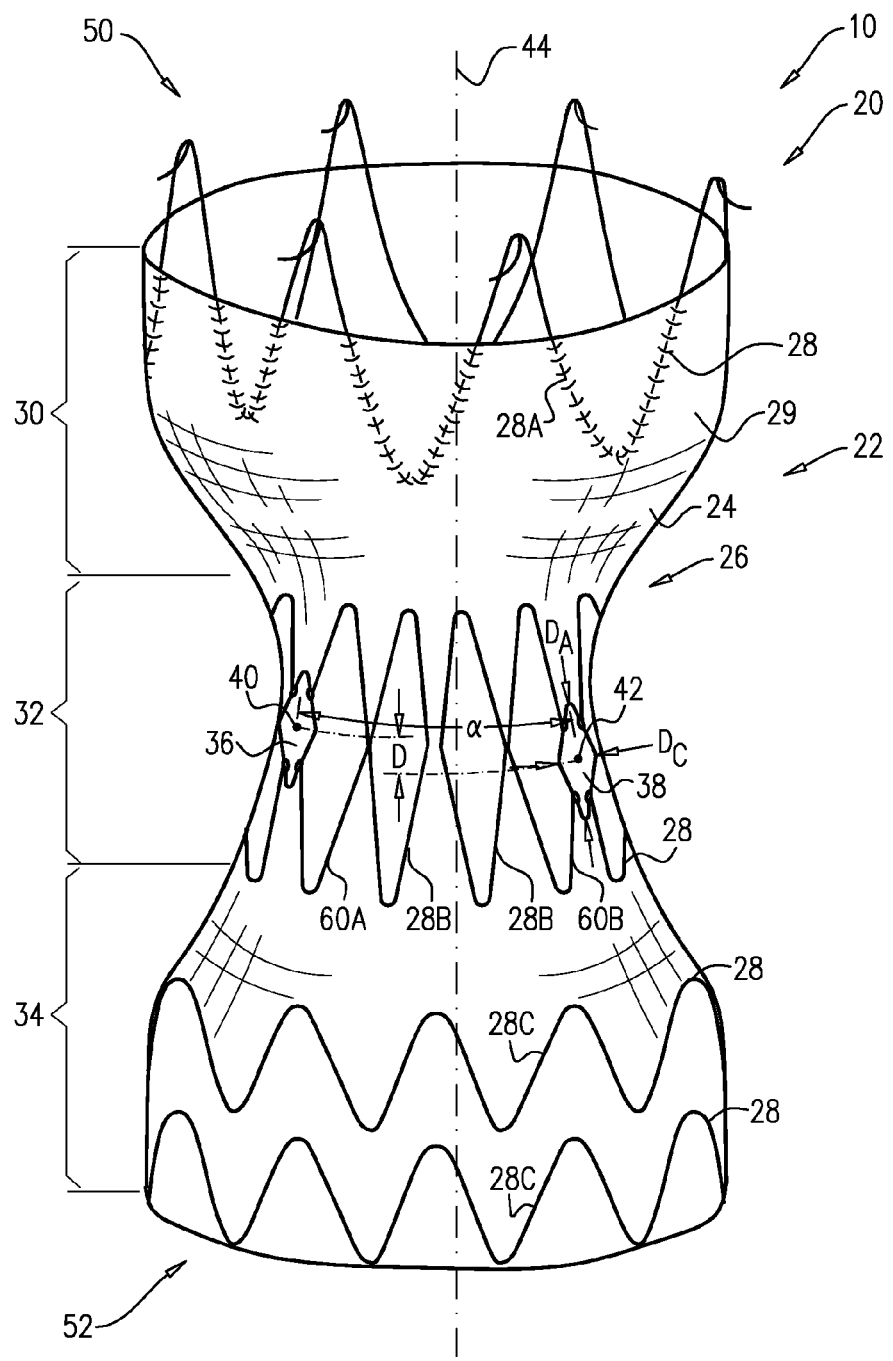
FIG. 1 is a schematic illustration of a main endovascular stent-graft, in accordance with an application of the present invention.

FIG. 1 is a schematic illustration of a main endovascular stent-graft 20, in accordance with an application of the present invention. Stent-graft 20 is one configuration of main endovascular stent-graft 10. Main endovascular stent-graft 20 comprises a generally tubular hourglass-shaped body 22, which is configured to initially be positioned in a delivery catheter in a radially-compressed delivery configuration, such as described hereinbelow with reference to FIG. 11A, and to assume a radially-expanded deployment configuration upon being deployed from the delivery catheter in a body lumen, such as a blood vessel, such as described hereinbelow with reference to FIGS. 11B-C. FIG. 1 shows the main endovascular stent-graft in the radially-expanded deployment configuration.

Main stent-graft 20 comprises a tubular fluid flow guide 24, and a flexible stent member 26, which comprises a plurality of structural stent elements 28. Fluid flow guide 24 is attached to structural stent elements 28, such as by suturing or stitching. Typically, each of stent elements 28 is shaped so as to define a plurality of stent cells. Structural stent elements 28 may be attached to an internal surface and/or an external surface of the fluid flow guide. Optionally, a portion of the structural stent elements may be attached (e.g., sutured) to the internal surface, and another portion to the external surface. For some applications, structural stent elements 28 comprise a metal. Alternatively or additionally, the structural stent elements comprise a self-expanding material, such that main stent-graft 20 is self-expandable. Alternatively or additionally, the structural stent elements comprise a superelastic metal alloy, a shape memory metallic alloy, and/or Nitinol. For some applications, the main stent-graft is heat-set to assume the radially-expanded configuration.

Fluid flow guide 24 comprises at least one piece of biologically-compatible substantially blood-impervious fabric 29. The fabric may comprise, for example, a polyester, a polyethylene (e.g., a poly-ethylene-terephthalate), a polymeric film material (e.g., polytetrafluoroethylene), a polymeric textile material (e.g., woven polyethylene terephthalate (PET)), natural tissue graft (e.g., saphenous vein or collagen), or a combination thereof.

Hourglass-shaped body 22 is shaped so as to define a narrow waist portion 32 longitudinally surrounded and adjacent to wider first and second longitudinal portions 30 and 34; waist portion 32 is longitudinally between and adjacent first and second portions 30 and 34. Waist portion 32, first longitudinal portion 30, and second longitudinal portion 34, when hourglass-shaped body 22 is in the radially-expanded deployment configuration, have:
- waist, first, and second average diameters, respectively;
- waist, first, and second smallest diameters, respectively;
- waist, first, and second greatest diameters, respectively;
- waist, first, and second average perimeters (which are circumferences for applications in which the portions are elliptical, e.g., circular, in cross-section), respectively;
- waist, first, and second smallest perimeters (which are circumferences for applications in which the portions are elliptical, e.g., circular, in cross-section), respectively; and
- waist, first, and second greatest perimeters (which are circumferences for applications in which the portions are elliptical, e.g., circular, in cross-section), respectively.

Typically, the diameters and perimeters of the first and second longitudinal portions vary at least partially therealong. Optionally, the diameter and perimeter of the waist portion vary at least partially therealong. As used in the present application, including in the claims, an "average" diameter or perimeter of a longitudinal portion means the average of the diameters or perimeters along the portion.

Typically, one or more first ones 28A of structural stent elements 28 are attached to fabric 29 along at least a portion of first longitudinal portion 30, one or more second ones 28B of structural stent elements 28 are attached to fabric 29 along at least a portion of waist portion 32, and one or more third ones 28C of structural stent elements 28 are attached to fabric 29 along at least a portion of second longitudinal portion 34. For some applications, none of the one or more first structural stent elements 28A is in direct contact with any of the one or more second structural stent elements 28B when hourglass-shaped body 22 is in the radially-expanded deployment configuration. Alternatively or additionally, for some applications, none of the one or more third structural stent elements 28C is in direct contact with any of the one or more second structural stent elements 28B when hourglass-shaped body 22 is in the radially-expanded deployment configuration. Alternatively or additionally, the one or more first structural stent elements are axially distant from the one or more second structural stent elements 28B when hourglass-shaped body 22 is in the radially-expanded deployment configuration. Alternatively or additionally, the one or more third structural stent elements are axially distant from the one or more second structural stent elements 28B when hourglass-shaped body 22 is in the radially-expanded deployment configuration.

For some applications, hourglass-shaped body 22 has an elliptical, e.g., circular, cross-section perpendicular to central longitudinal axis 44, when hourglass-shaped body 22 is in the radially-expanded deployment configuration. For some applications, first longitudinal portion 30 has an elliptical, e.g., circular, cross-section perpendicular to central longitudinal axis 44, when hourglass-shaped body 22 is in the radially-expanded deployment configuration. For some applications, first longitudinal portion 30 is shaped so as to define an outflaring at at least one of its ends, typically at its first (superior) end, which outflaring may increase radial strength and hence improving apposition with the landing zone upon the healthy region in the artery and inhibit migration of the prosthesis. For some applications, waist portion 32 has an elliptical, e.g., circular, cross-section perpendicular to central longitudinal axis 44, when hourglass-shaped body 22 is in the radially-expanded deployment configuration. For some applications, waist portion 32 is shaped so as to define an outflaring at at least one of its ends. For some applications, waist portion 32 has an elliptical cross-section having a larger diameter in the sagittal plane and a smaller diameter in the coronal plane. For some applications, second portion 34 has an elliptical, e.g., circular, cross-section perpendicular to central longitudinal axis 44, when hourglass-shaped body 22 is in the radially-expanded deployment configuration. For some applications, second longitudinal portion 34 is shaped so as to define an outflaring at at least one of its ends.

For some applications, waist portion 32 is shaped so as to define a constant diameter cylinder when the hourglass-shaped body is in the radially-expanded deployment configuration. Alternatively, for some applications, the waist portion is shaped so as to define a radially concave tube when the hourglass-shaped body is in the radially-expanded deployment configuration. Further alternatively, for some applications, contoured such that it has a groove having the shape of an inward facing trapezoid (wherein the smaller base is more medial and the larger base constitutes a continuum with one of the larger diameters, of either the first or the second portion), when the hourglass-shaped body is in the radially-expanded deployment configuration.

Fabric 29 along waist portion 32 is shaped so as to define at least first and second lateral apertures 36 and 38. In addition, typically one or more of structural stent elements 28 attached to fabric 29 along at least a portion of waist portion 32 are shaped so as to define first and second lateral apertures 36 and 38, respectively (i.e., to define respective borders of the apertures), when hourglass-shaped body 22 is in the radially-expanded deployment configuration, in order to provide structure to the borders and thus good fixation with branching stent-grafts, as described hereinbelow. Typically, one of structural stent elements 28 (e.g., a stent cell thereof) also defines first lateral aperture 36, and one of structural stent elements 28 (e.g., a stent cell thereof) also defines second lateral aperture 38. These lateral apertures are configured for coupling to branching stent-grafts, such as described hereinbelow with reference to FIGS. 7-9 and FIGS. 11C-E. Typically, first and second lateral apertures 36 and 38 are disposed such that an arc angle α (alpha) around a central longitudinal axis 44 of hourglass-shaped body 22 between respective centers 40 and 42 of the first and the second lateral apertures is between 120 and 180 degrees, such as between 130 and 170 degrees, e.g., 150 degrees, when hourglass-shaped body 22 is in the radially-expanded deployment configuration. The ostia of the renal arteries are on average about 150 degrees apart, so the arc angles of the apertures help the main stent-graft accommodate the locations of typical ostia, as described hereinbelow. Typically, an axial distance D between respective centers 40 and 42 of first and second lateral apertures 36 and 38, measured along central longitudinal axis 44, is no more than 2 cm.

For some applications, each of first and second lateral apertures 36 and 38 has a perimeter (which is a circumference if the apertures are elliptical, e.g., circular) of at least 12 mm, no more than 150 mm, and/or between 12 and 150 mm. For some applications, each of first and second lateral apertures 36 and 38 has a diameter of at least 6 mm, no more than 15 mm, and/or between 6 and 15 mm. For some applications, each of first and second lateral apertures 36 and 38 has an axial diameter $D_A$, measured along central longitudinal axis 44, of at least 4 mm, no more than 12 mm, and/or between 4 and 12 mm, and/or a circumferential diameter $D_C$, measured around central longitudinal axis 44, of at least 4 mm, no more than 12 mm, and/or between 4 and 12 mm. For some applications, a ratio between the second average diameter and the diameter of each of the lateral apertures is between 1.3 and 6. For some applications, a ratio between the first average diameter and the diameter of each of the lateral apertures is between 1.5 and 7. For some applications, a ratio between the waist average diameter and the diameter of each of the lateral apertures is between 1 and 5.

For some applications, the first average diameter is at least 25 mm, no more than 40 mm, and/or between 25 and 40 mm. For some applications, a greatest diameter of first longitudinal portion 30, which may occur at a first end 50 of hourglass-shaped body 22, as well as at other longitudinal locations along the first portion, is at least 30 mm, no more than 45 mm, and/or between 30 and 45 mm. For some applications, the first average perimeter is at least 78 mm, no more than 125 mm, and/or between 78 and 125 mm. For some applications, a greatest perimeter of first longitudinal portion 30, which may occur at a first end 50 of hourglass-shaped body 22, as well as at other longitudinal locations along the first portion, is at least 94 mm, no more than 141 mm, and/or between 94 and 141 mm.

For some applications, the waist average diameter is at least 15 mm, no more than 30 mm, and/or between 15 and 30 mm. For some applications, a greatest diameter of waist portion 32 is at least 20 mm, no more than 35 mm, and/or between 20 and 35 mm. For some applications, a smallest diameter of waist portion 32 is at least 13 mm, no more than 25 mm, and/or between 13 and 25 mm. For some applications, the waist average perimeter is at least 47 mm, no more than 94 mm, and/or between 47 and 94 mm. For some applications, a greatest perimeter of waist portion 32 is at least 63 mm, no more than 110 mm, and/or between 63 and 110 mm. For some applications, a smallest perimeter of waist portion 32 is at least 41 mm, no more than 78 mm, and/or between 41 and 78 mm.

For some applications, the second average diameter is at least 20 mm, no more than 35 mm, and/or between 20 and 35 mm. For some applications, a greatest diameter of second longitudinal portion 34, which may occur at a second end 52 of hourglass-shaped body 22, as well as at other longitudinal locations along the second longitudinal portion, is at least 25 mm, no more than 40 mm, and/or between 25 and 40 mm. For some applications, the second average perimeter is at least 63 mm, no more than 110 mm, and/or between 63 and 110 mm. For some applications, a greatest perimeter of second longitudinal portion 34, which may occur at a second end 52 of hourglass-shaped body 22, as well as at other longitudinal locations along the second portion, is at least 78 mm, no more than 125 mm, and/or between 78 and 125 mm.

Hourglass-shaped body 22 is hourglass-shaped; in other words, waist portion 32 is narrower than first and second longitudinal portions 30 and 34. Typically:

- the waist average diameter is at least 60%, no more than 90%, and/or between 60% and 90% of the lesser of the first and the second average diameters, such as between 70% and 80% of the lesser of the first and the second average diameters. For some applications, the waist average diameter is at least 60%, no more than 90%, and/or between 60% and 90% of each of the first and the second average diameters (taken separately), such as between 70% and 80% of each of the first and the second average diameters (taken separately);
- the waist smallest diameter is at least 60%, no more than 90%, and/or between 60% and 90% of the lesser of the first and the second greatest diameters, such as between 70% and 80% of the lesser of the first and the second greatest diameters. For some applications, the waist smallest diameter is at least 60%, no more than 90%, and/or between 60% and 90% of each of the first and the second greatest diameters (taken separately), such as between 70% and 80% of each of the first and the second greatest diameters (taken separately);
- the waist average perimeter is at least 60%, no more than 90%, and/or between 60% and 90% of the lesser of the first and the second average perimeters, such as between 70% and 80% of the lesser of the first and the second average perimeters. For some applications, the waist average perimeter is at least 60%, no more than 90%, and/or between 60% and 90% of each of the first and the second average perimeters (taken separately), such as between 70% and 80% of each of the first and the second average perimeters (taken separately); and/or
- the waist smallest perimeter is at least 60%, no more than 90%, and/or between 60% and 90% of the lesser of the first and the second greatest perimeters, such as between 70% and 80% of the lesser of the first and the second greatest perimeters. For some applications, the waist smallest perimeter is at least 60%, no more than 90%, and/or between 60% and 90% of each of the first and the second greatest perimeters (taken separately), such as between 70% and 80% of each of the first and the second greatest perimeters (taken separately).

For some applications, when hourglass-shaped body 22 is in the radially-expanded deployment configuration, (a) narrow waist portion 32 has coronal and sagittal waist diameters, and an average waist diameter thereof, (b) first longitudinal portion 30 has coronal and sagittal first diameters, and an average first diameter thereof, (c) second longitudinal portion 34 has coronal and sagittal second diameters, and an average second diameter thereof, and (d) the average waist diameter equals at least 60% of, no more than 90% of, and/or between 60% and 90% of the lesser of the average first diameter and the average second diameter.

The axial and circumferential locations of the ostia of arteries that branch from the aorta vary substantially from patient to patient. These arteries include the left and right renal arteries, the celiac artery, and the superior mesenteric artery (SMA). The hourglass shape of main stent-graft 20 enables the main stent-graft to accommodate this varying anatomy, without requiring customization of the main stent-graft for each patient to align the lateral apertures with the patient's ostia. As described hereinbelow with reference to FIGS. 11C-E, branching stent-grafts are coupled to the lateral apertures after main stent-graft 20 has been deployed in the aorta. The hourglass shape provides space between the lateral apertures and the ostia, in which space the surgeon can manipulate the branching stent-grafts in order to accommodate any axial or circumferential misalignment between the lateral apertures and the ostia. Typically, the hourglass shape enables the main stent-graft to accommodate up to about 1 cm in axial misalignment between the lateral apertures and the respective ostia of the branching vessels.

First, waist, and second longitudinal portions 30, 32, and 34 have respective longitudinal lengths L1, L2, and L3. Typically, each of these lengths is at least 20 mm. For some applications, L1 is at least 15 mm, no more than 50 mm, and/or between 15 and 50 mm, L2 is at least 20 mm, no more than 70 mm, and/or between 20 and 70 mm, and L3 is at least 10 mm, no more than 100 mm, and/or between 10 and 100 mm.

For some applications, the one or more second structural stent elements 28B of waist portion 32 comprise first and second stent elements 60A and 60B, which are shaped so as to define first and second lateral apertures 36 and 38, respectively, when hourglass-shaped body 22 is in the radially-expanded deployment configuration. In general, the smaller (e.g., shorter) the metal stent elements (i.e., struts) are, the less likely they are to fracture. Therefore, providing two separate stent elements 60A and 60B provides columnar support similar to that provided by a single stent element, with an average of ½ to ⅔ of the length the stent elements would have if provided as a single stent element shaped as to provide both the first and the second lateral apertures. For some applications, when hourglass-shaped body 22 is in the radially-expanded deployment configuration, a stent cell of stent element 60A defines first lateral aperture 36, and a stent cell of stent element 60B defines first lateral aperture 38. For some applications, stent elements 60A and 60B are shaped so as define respective closed-cell orifices characterized by respective centers, and wherein the centers generally coincide with centers 40 and 42 of first and second lateral apertures 36 and 38, respectively, when hourglass-shaped body 22 is in the radially-expanded deployment configuration. Typically, first and second stent elements 60A and 60B are not in direct contact with each other when hourglass-shaped body 22 is in the radially-expanded deployment configuration.

For some applications, when hourglass-shaped body 22 is in the radially-expanded configuration, first and second stent elements 60A and 60B axially overlap and do not circumferentially overlap, such as shown in FIG. 1, while for other applications, first and second stent elements 60A and 60B circumferentially overlap, such as described hereinbelow with reference to FIG. 3. For some applications, each of first and second stent elements 60A and 60B circumscribes an arc angle of at least 50 degrees, no more than 170 degrees, and/or between 50 and 170 degrees, when hourglass-shaped body 22 is in the radially-expanded deployment configuration.

Figure 2:
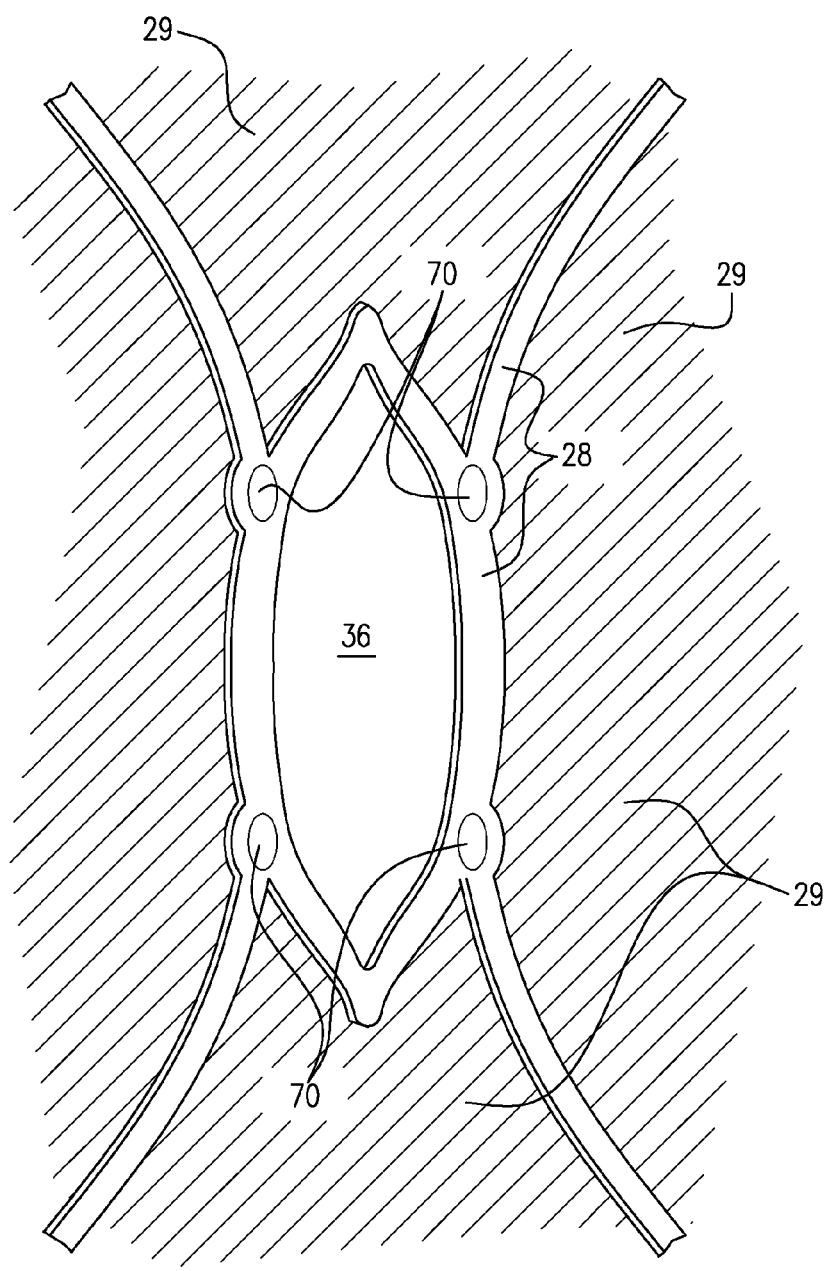
FIG. 2 is a schematic illustration of a first lateral aperture of the main stent-graft of FIG. 1 and a surrounding portion of the main stent-graft, in accordance with an application of the present invention.

Reference is made to FIG. 2, which is a schematic illustration of first lateral aperture 36 and a surrounding portion of main stent-graft 20, in accordance with an application of the present invention. FIG. 2 shows the main stent-graft in the radially-expanded deployment configuration. In this configuration, one or more radiopaque markers 70 are disposed around the perimeter of first lateral aperture 36. For example, the radiopaque markers may be coupled to the portion of structural stent element 28 that surrounds and defines first lateral aperture 36, such as two at each side of the aperture. Radiopaque markers may similarly be provide for second lateral aperture 38. The radiopaque markers aid the surgeon during insertion of the guiding catheters, and/or guidewires, and/or subsequently, the branching stent-grafts into the lateral apertures, such as described hereinbelow with reference to FIG. 11C.

Figure 3:
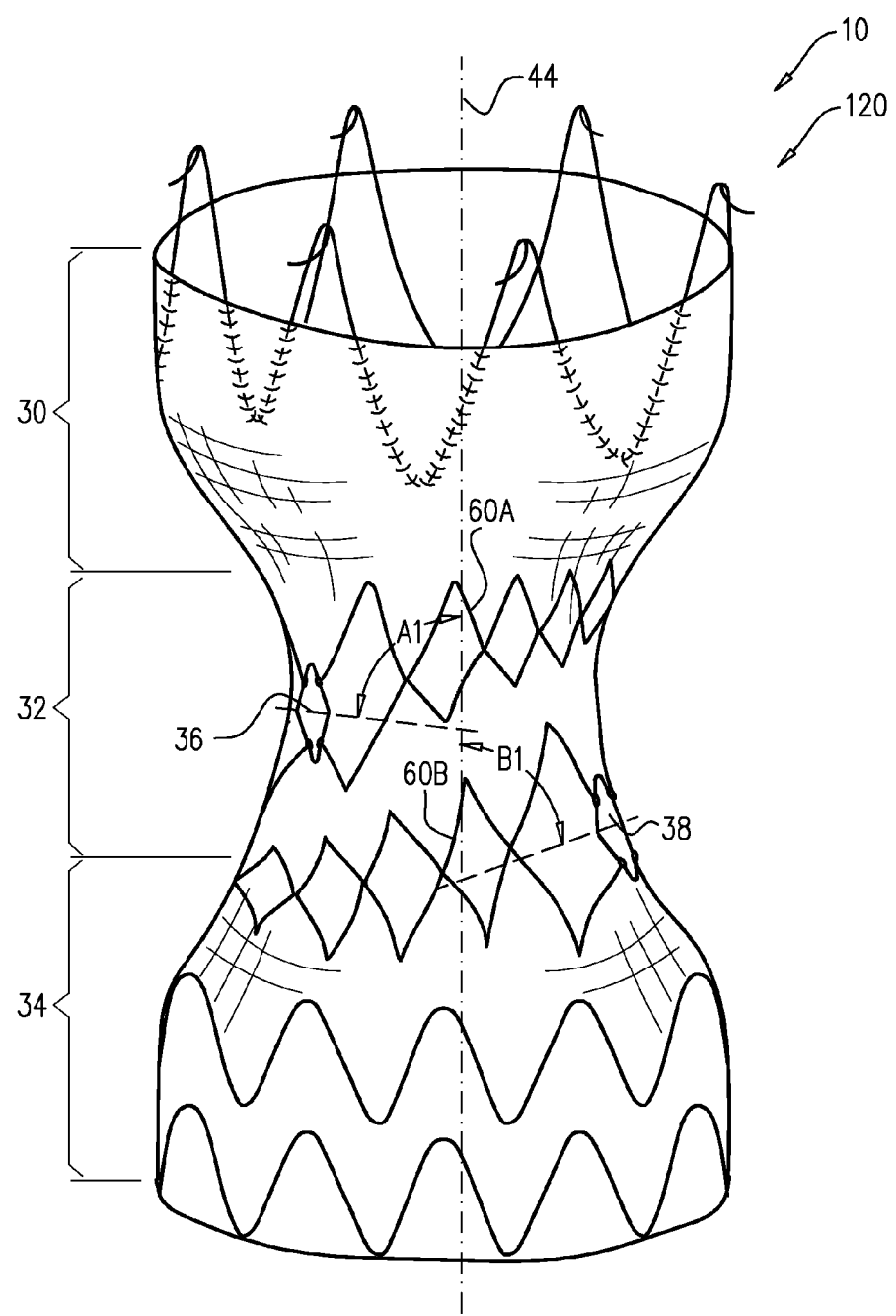
FIG. 3 is a schematic illustration of another main endovascular stent-graft, in accordance with an application of the present invention.

Reference is now made to FIG. 3, which is a schematic illustration of a main endovascular stent-graft 120, in accordance with an application of the present invention. Main stent-graft 120 is one configuration of main endovascular stent-graft 10. Other than as described hereinbelow, main endovascular stent-graft 120 is generally similar to main stent-graft 20, described hereinabove with reference to FIG. 1, and may incorporate the features of main stent-graft 20. FIG. 3 shows the main stent-graft in the radially-expanded deployment configuration. In this configuration, first and second stent elements 60A and 60B circumferentially overlap when hourglass-shaped body 22 is in the radially-expanded deployment configuration. Typically, the first and the second stent elements are axially separated therebetween when hourglass-shaped body 22 is in the radially-expanded deployment configuration.

For some applications, the first stent element is shaped substantially as an axial inversion of the second stent element when the hourglass-shaped body is in the radially-expanded deployment configuration. Alternatively or additionally, for some applications, the first and the second stent elements are shaped so as to define respective trapezoids when the hourglass-shaped body is in the radially-expanded deployment configuration. For some applications, the trapezoids are right trapezoids, as shown in FIGS. 3-6. Alternatively, for some applications, the first and the second stent elements are shaped so as to define right triangles when the hourglass-shaped body is in the radially-expanded deployment configuration.

For some applications, when the hourglass-shaped body is in the radially-expanded deployment configuration, first and second stent elements 60A and 60B circumferentially overlap, axially overlap (such as shown in FIG. 1, or both circumferentially and axially overlap (such as shown in FIG. 3, and FIGS. 4, 5, and 10A-B).

Figure 4:
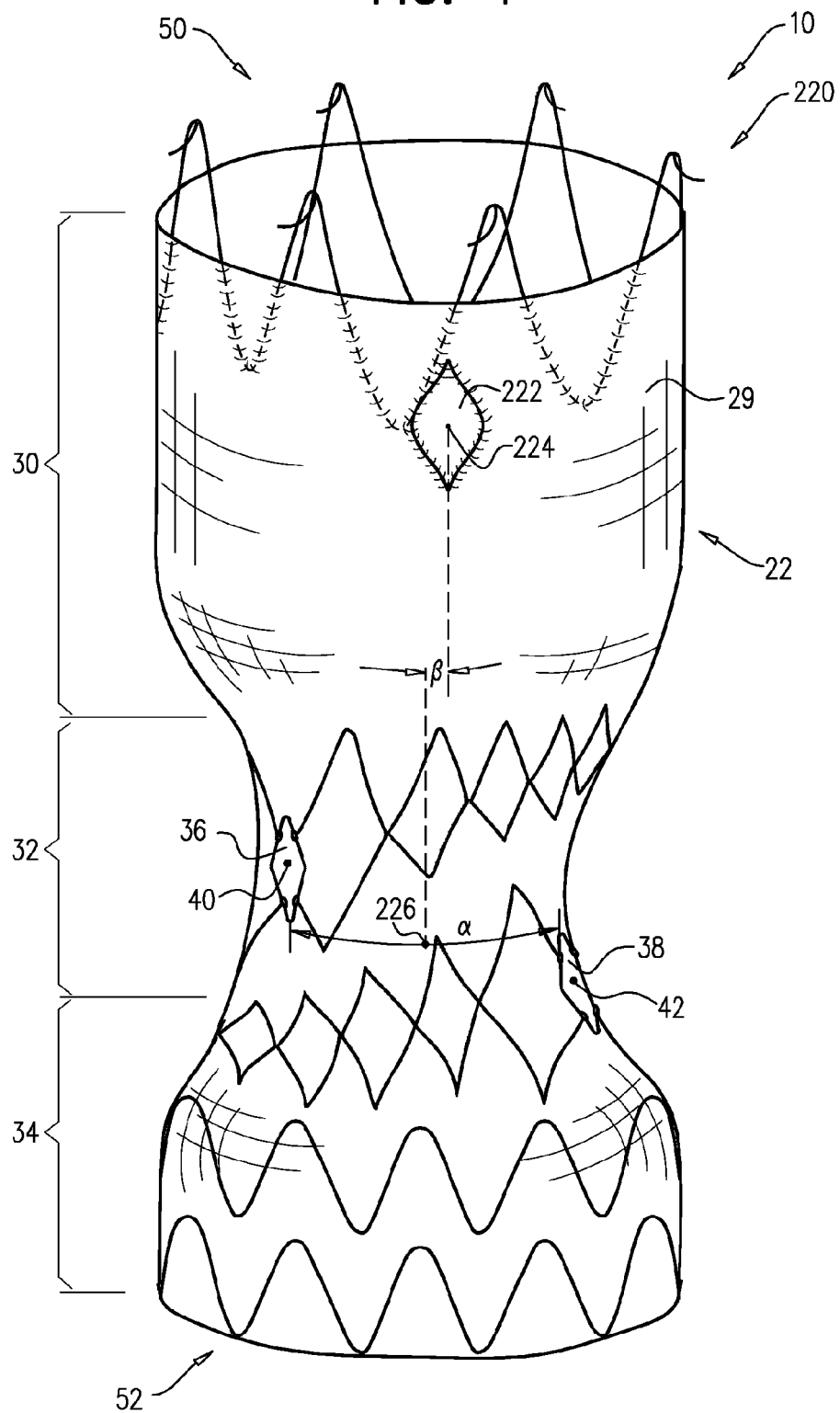
FIG. 4 is a schematic illustration of yet another main endovascular stent-graft, in accordance with an application of the present invention.

Reference is now made to FIG. 4, which is a schematic illustration of a main endovascular stent-graft 220, in accordance with an application of the present invention. Main stent-graft 220 is one configuration of main endovascular stent-graft 10. Other than as described hereinbelow, main endovascular stent-graft 220 is generally similar to main stent-graft 20, described hereinabove with reference to FIG. 1, and/or main stent-graft 120, described hereinabove with reference to FIG. 3, and may incorporate the features of main stent-graft 20 and/or main stent-graft 120. FIG. 4 shows the main stent-graft in the radially-expanded deployment configuration. Although the stent elements of waist portion 32 are shown with the configuration of main stent-graft 120, these stent elements may instead have the configuration of main stent-graft 20, or other configurations.

Fabric 29 along first portion 30 is shaped so as to define a superior aperture 222. In addition, typically one or more of structural stent elements 28 attached to fabric 29 along at least a portion of first longitudinal portion 30 are shaped so as to define superior aperture 222, i.e., to define the border thereof, in order to provide structure to the border and thus good fixation with a branching stent-graft, as described hereinbelow. This lateral aperture is configured for coupling to a branching stent-graft to the superior mesenteric artery (SMA). For some applications, superior aperture 222 is disposed so as to define a superior aperture arc angle β (beta) around the central longitudinal axis between (a) a center 224 of superior aperture 222 and (b) a midpoint 226 of arc angle α (alpha) between respective centers 40 and 42 of first and second lateral apertures 36 and 38, superior aperture arc β (beta) angle being less than 60 degrees when hourglass-shaped body 22 is in the radially-expanded deployment configuration. For some applications, a perimeter (which is a circumference if the aperture is elliptical, e.g., circular) of superior aperture 222 is at least 15 mm, no more than 30 mm, and/or between 15 and 30 mm.

Figure 5:
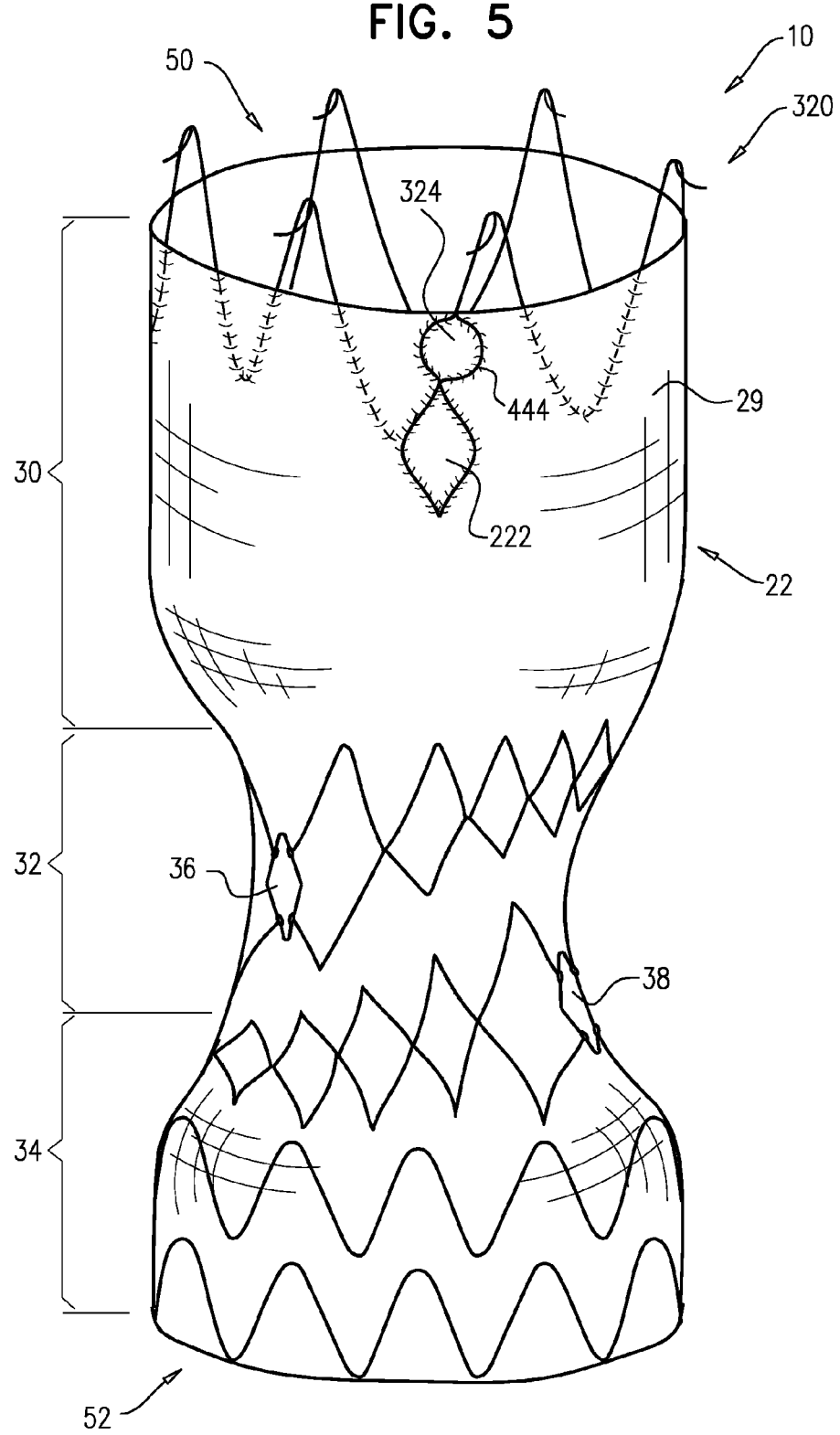
FIG. 5 is a schematic illustration of still another main endovascular stent-graft, in accordance with an application of the present invention.

Reference is now made to FIG. 5, which is a schematic illustration of a main endovascular stent-graft 320, in accordance with an application of the present invention. Main stent-graft 320 is one configuration of main endovascular stent-graft 10. Other than as described hereinbelow, main endovascular stent-graft 320 is generally similar to main stent-graft 220, described hereinabove with reference to FIG. 3, and may incorporate the features of main stent-grafts 20, 120, and/or 220. FIG. 5 shows the main stent-graft in the radially-expanded deployment configuration. Although the stent elements of waist portion 32 are shown with the configuration of main stent-graft 120, these stent elements may instead have the configuration of main stent-graft 20, or other configurations.

As in the configuration described hereinabove with reference to FIG. 4, fabric 29 along first portion 30 is shaped so as to define superior aperture 222. This lateral aperture is configured for coupling to a branching stent-graft to the superior mesenteric artery (SMA). Superior aperture 222 may be disposed as described hereinabove with reference to FIG. 4, and may have the perimeter described hereinabove with reference to FIG. 4.

In addition, fabric 29 along first portion 30 is shaped so as to define a secondary superior aperture 324 (in which case superior aperture 222 serves as a primary superior aperture). In addition, typically one or more of structural stent elements 28 attached to fabric 29 along at least a portion of first longitudinal portion 30 are shaped so as to define secondary superior aperture 324, i.e., to define the border thereof, in order to provide structure to the border and thus good fixation with a branching stent-graft, as described hereinbelow. This superior aperture is configured for coupling a branching stent-graft to the celiac artery. Secondary superior aperture 324 is typically slightly (e.g., between 8 and 20 mm) closer to first end 50 than primary superior aperture 222 is to the first end, and is typically circumferentially aligned with primary superior aperture 222. For some applications, a perimeter (which is a circumference if the aperture is elliptical, e.g., circular) of secondary superior aperture 324 is at least 3 mm, no more than 6 mm, and/or between 3 and 6 mm.

Figure 6:
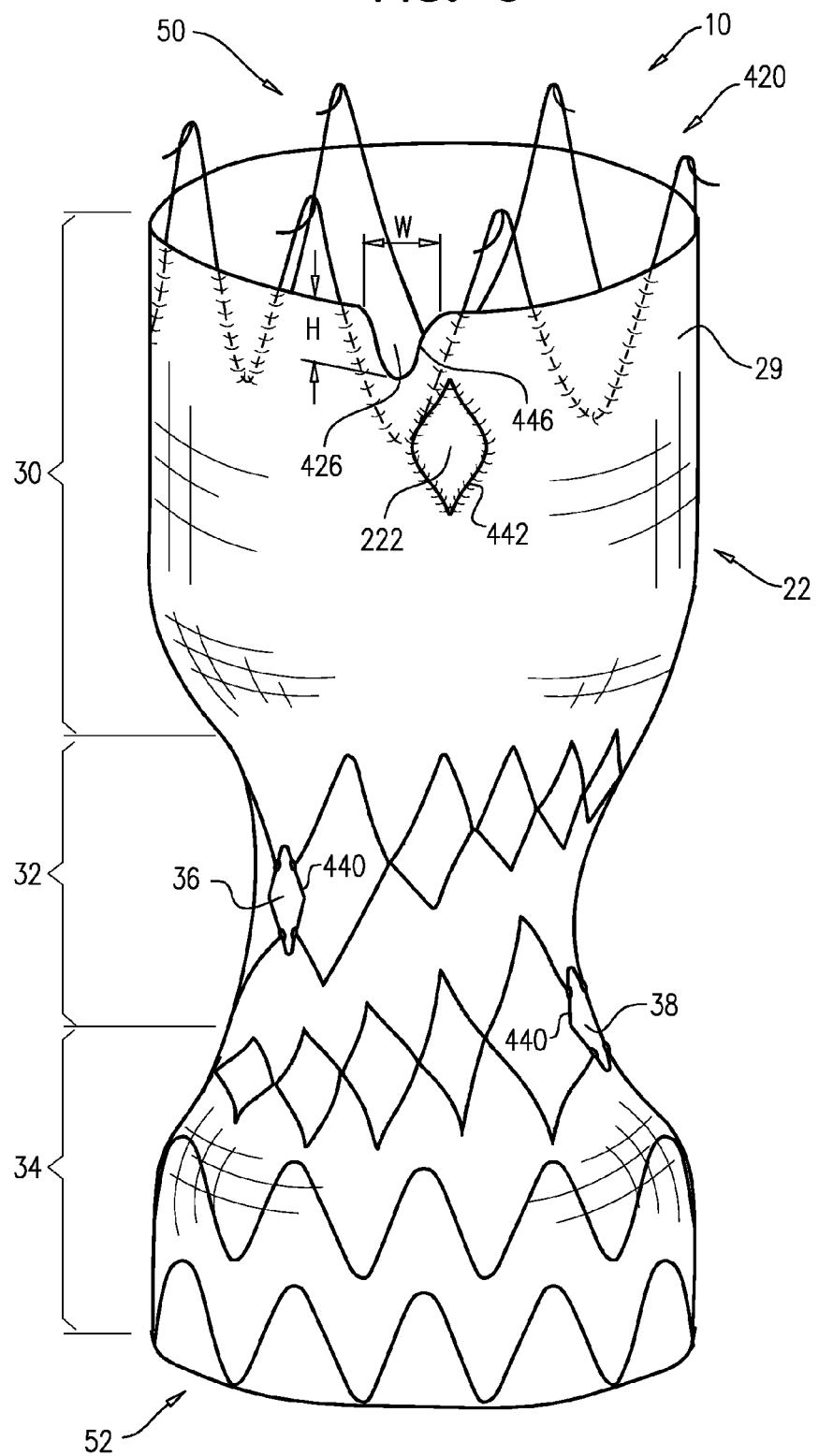
FIG. 6 is a schematic illustration of another endovascular stent-graft, in accordance with an application of the present invention.

Reference is now made to FIG. 6, which is a schematic illustration of a main endovascular stent-graft 420, in accordance with an application of the present invention. Main stent-graft 420 is one configuration of main endovascular stent-graft 10. Other than as described hereinbelow, main endovascular stent-graft 420 is generally similar to main stent-graft 220, described hereinabove with reference to FIG. 3, and may incorporate the features of main stent-grafts 20, 120, 220, and/or 320. FIG. 6 shows the main stent-graft in the radially-expanded deployment configuration. Although the stent elements of waist portion 32 are shown with the configuration of main stent-graft 120, these stent elements may instead have the configuration of main stent-graft 20, or other configurations.

As in the configuration described hereinabove with reference to FIG. 4, fabric 29 along first portion 30 is shaped so as to define superior aperture 222. This lateral aperture is configured for coupling to a branching stent-graft to the superior mesenteric artery (SMA). Superior aperture 222 may be disposed as described hereinabove with reference to FIG. 4, and may have the perimeter described hereinabove with reference to FIG. 4.

In addition, fabric 29 along first longitudinal portion 30 is shaped so as to define a superior scallop 426, which is open to and extends away from an edge of fabric 29. In addition, for some applications, one or more of structural stent elements 28 attached to fabric 29 along at least a portion of first longitudinal portion 30 are shaped so as to define superior scallop 426, i.e., to define the border thereof. Superior scallop 426 is configured to allow free blood flow to the celiac artery. Superior scallop 426 typically begins at first end 50 and ends between 10 to 30 mm inferiorly to first end 50. For some applications, a width W of superior scallop 426, measured in a circumferential direction, is at least 10 mm, no more than 20 mm, and/or between 10 and 20 mm, such as at least 5 mm, no more than 12 mm, and/or between 5 and 12 mm, and a height H of superior scallop 426, measured in a direction parallel with central longitudinal axis 44, is at least 5 mm, no more than 30 mm, and/or between 5 and 30 mm, such as at least 5 mm (e.g., at least 10 mm), no more than 25 mm, and/or between 5 mm (e.g., 10 mm) and 25 mm. For some applications, superior scallop 426 is generally shaped as a semi-circle. For some applications, superior scallop 426 is disposed so as to define a superior scallop arc angle around central longitudinal axis 44 between (a) a center of superior scallop 426 and (b) a midpoint of an arc angle between respective centers of first and the second lateral apertures 36 and 38, the superior scallop arc angle being less than 60 degrees when hourglass-shaped body 22 is in the radially-expanded deployment configuration.

Reference is still made to FIG. 6. As mentioned above, typically one or more of structural stent elements 28 attached to fabric 29 along at least a portion of waist portion 32 are shaped so as to define first and second lateral apertures 36 and 38, respectively, when hourglass-shaped body 22 is in the radially-expanded deployment configuration. For some applications, the one or more structural stent elements 28 that define one or more of the apertures, i.e., respective borders thereof, comprise respective radiopaque wires 440. These radiopaque structural stent elements thus both provide structure to the apertures (for fixation of branching stent-grafts therein) and visualization of the aperture during imaging, typically fluoroscopy. The radiopaque borders of the apertures aid the surgeon during insertion of the guiding catheters, and/or guidewires, and/or subsequently, the branching stent-grafts into the lateral apertures, such as described hereinbelow with reference to FIG. 11C. These techniques may be implemented in combination with any of the configurations of main stent-graft 10 described herein, such as with reference to FIGS. 1, 3, 4, 5, 6, and 10A-C.

Similarly, for some applications in which one or more of structural stent elements 28 attached to fabric 29 along at least a portion of first longitudinal portion 30 are shaped so as to define superior aperture 222, i.e., to define the border thereof, these one or more structural stent elements 28 comprise respective radiopaque wires 442.

Similarly, for some applications in which one or more of structural stent elements 28 attached to fabric 29 along at least a portion of first longitudinal portion 30 are shaped so as to define secondary superior aperture 324, i.e., to define the border thereof, as described hereinabove with reference to FIG. 5, these one or more structural stent elements 28 comprise respective radiopaque wires 444.

Similarly, for some application in which one or more of structural stent elements 28 attached to fabric 29 along at least a portion of first longitudinal portion 30 are shaped so as to define superior scallop 426, i.e., to define the border thereof, these one or more structural stent elements 28 comprise respective radiopaque wires 446.

Typically, radiopaque wires 440, 442, 444, and 446 comprise a metal, such as tungsten, gold, titanium, or iridium. Typically, structural stent elements 28, other than radiopaque wires 440, 442, 444, and 446 that define the one or more apertures, are less radiopaque than the radiopaque wires. For example, these other structural stent elements may comprise Nitinol, stainless steel, or cobalt chromium. For some applications, a collective mass of the structural stent elements 28, other radiopaque wires 440, 442, 444, and 446, equals at least 10 times a collective mass of radiopaque wires 440, 442, 444, and 446.

Reference is now made to FIGS. 7-9, which are schematic illustrations of several configurations of branching endovascular stent-grafts 500, in accordance with respective applications of the present invention. Branching stent-grafts 500 are configured to be coupled to first and second lateral apertures 36 and 38 of main stent-graft 10, such as described hereinbelow with reference to FIGS. 11C-E. FIGS. 7-9 show the branching stent-grafts in radially-expanded deployment configurations. Branching stent-grafts 500 are configured to initially be positioned in a delivery catheter in radially-compressed delivery configurations (not shown).

Each of branching stent-grafts 500 comprises a tubular fluid flow guide 532, and a flexible stent member 530, which comprises a plurality of structural stent elements (a portion of which are hidden by fluid flow guide 532 in FIGS. 7-9). Fluid flow guide 532 is attached to the structural stent elements, such as by suturing or stitching. Each of branching stent-grafts 500 has a first end 520, which is configured to be coupled to the lateral apertures of main stent-graft 10, and an opposite second end 522.

Typically, each of the structural stent elements is shaped so as to define a plurality of stent cells. The structural stent elements may be attached to an internal surface and/or an external surface of the fluid flow guide. Optionally, a portion of the structural stent elements may be attached (e.g., sutured) to the internal surface, and another portion to the external surface. For some applications, the structural stent elements comprise a metal. Alternatively or additionally, the structural stent elements comprise a self-expanding material, such that stent-graft 500 is self-expandable. Alternatively or additionally, the structural stent elements comprise a superelastic metal alloy, a shape memory metallic alloy, and/or Nitinol. For some applications, the stent-graft is heat-set to assume the radially-expanded configuration.

Fluid flow guide 532 comprises at least one piece of biologically-compatible substantially blood-impervious fabric 534. The fabric may comprise, for example, a polyester, a polyethylene (e.g., a poly-ethylene-terephthalate), a polymeric film material (e.g., polytetrafluoroethylene), a polymeric textile material (e.g., woven polyethylene terephthalate (PET)), natural tissue graft (e.g., saphenous vein or collagen), or a combination thereof.

Each of branching stent-grafts 500 is shaped so as to define an interface portion 542 near first end 520 thereof, e.g., within 5 mm of the first end. When the branching stent-graft is in the radially-expanded deployment configuration, the interface portion is shaped so as to define a stricture 540, i.e., a narrow portion, on either longitudinal side of which the stent-graft is wider. Stricture 540 is sized and shaped to be placed within, and securely interface with, one of first and second lateral apertures 36 and 38, so as to form a blood-tight seal with the perimeter of the lateral aperture. The structural stent elements of flexible stent member 530 help define stricture 540, and thus provide a solid structural interface with the lateral aperture, as well as some tolerance to deployment positioning errors by the operators, as the slopes on each side of stricture 540 tend to centralize the narrowest portion of the stricture at a plane similar to that of lateral apertures 36 and 38 or the primary or secondary superior apertures. When the branching stent-graft is in the radially-expanded deployment configuration, a portion of the structural stent elements of interface portion 432 extends beyond stricture 540 toward first end 520 of the branching stent-graft, and radially outward, in order to provide good coupling of the interface portion with one of first and second lateral apertures 36 and 38.

When coupled to one of the lateral apertures, interface portion 542 typically extends radially inward into the lumen of the main stent-graft only slightly, such as by no more than 5 mm, e.g., no more than 3 mm, e.g., between 2 and 5 mm, such that interface portion 542 does not substantially interfere with blood flow through the lumen. For example, fabric 534 may extend by no more than 0.5 mm, and stent member 530 may extend by no more than 1 mm into the lumen of the main stent-graft. Such non-interference with blood flow allows the main stent-graft to have narrower waist portion 32, and yet still provide sufficient blood flow through the lumen of this narrower portion, which would not be possible if the interface portions of two or three branching stent-grafts extended too far into the lumen of the main stent-graft.

For some applications, a diameter of the branching stent graft generally monotonously does not decrease from second end 522 to first end 520 of the branching stent-graft. For some applications, the diameter at first end 520 is at least 20% greater than the diameter at second end 522. For some applications, a diameter of the branching structural stent elements adjacently distal the stricture is at least 5% greater than a diameter of the branching fabric at the same longitudinal location along the branching stent graft, when the first branching stent-graft is in the branching radially-expanded deployment configuration. In other words, there is some oversizing between flexible stent member 530 and fluid flow guide 532 so that the stent member is capable of outwardly pressing against the fabric of the fluid flow guide when they are attached to each other.

FIG. 7 is a schematic illustration of a branching stent-graft 510, in accordance with an application of the present invention. Branching stent-graft 510 is one configuration of branching stent-graft 500. In this configuration, fabric 534 of fluid flow guide 532 at least partially covers, and is securely attached to, the structural stent elements of interface portion 432 that extend beyond stricture 540 toward first end 520 of the branching stent-graft, when the branching stent-graft is in the radially-expanded deployment configuration.

FIG. 8 is a schematic illustration of a branching stent-graft 610, in accordance with an application of the present invention. Branching stent-graft 610 is one configuration of branching stent-graft 500. In this configuration, fabric 534 of fluid flow guide 532 does not cover the structural stent elements of interface portion 432 that extend beyond stricture 540 toward first end 520 of the branching stent-graft, when the branching stent-graft is in the radially-expanded deployment configuration.

FIG. 9 is a schematic illustration of a branching stent-graft 710, in accordance with an application of the present invention. Branching stent-graft 710 is one configuration of branching stent-graft 500. In this configuration, the structural stent elements of interface portion 542 comprise:

first structural stent elements 544, which extend from stricture 540 and beyond stricture 540 toward first end 520 of the branching stent-graft, and radially outward, when the branching stent-graft is in the radially-expanded deployment configuration; fabric 534 typically does not cover first structural stent elements 544;

second structural stent elements 546, which extend from stricture 540 toward second end 522 of the branching stent-graft, and radially outward, when the branching stent-graft is in the radially-expanded deployment configuration; fabric 534 typically does not cover second structural stent elements 546; and optionally, third structural stent elements 548, which extend from stricture 540 toward second end 522 of the branching stent-graft, and are generally aligned with a surface of fabric 534, when the branching stent-graft is in the radially-expanded deployment configuration. Third structural stent elements 548 are coupled to third structural stent elements 548, such by stitching, and help support the fabric of the branching stent-graft.

Figure 10A:
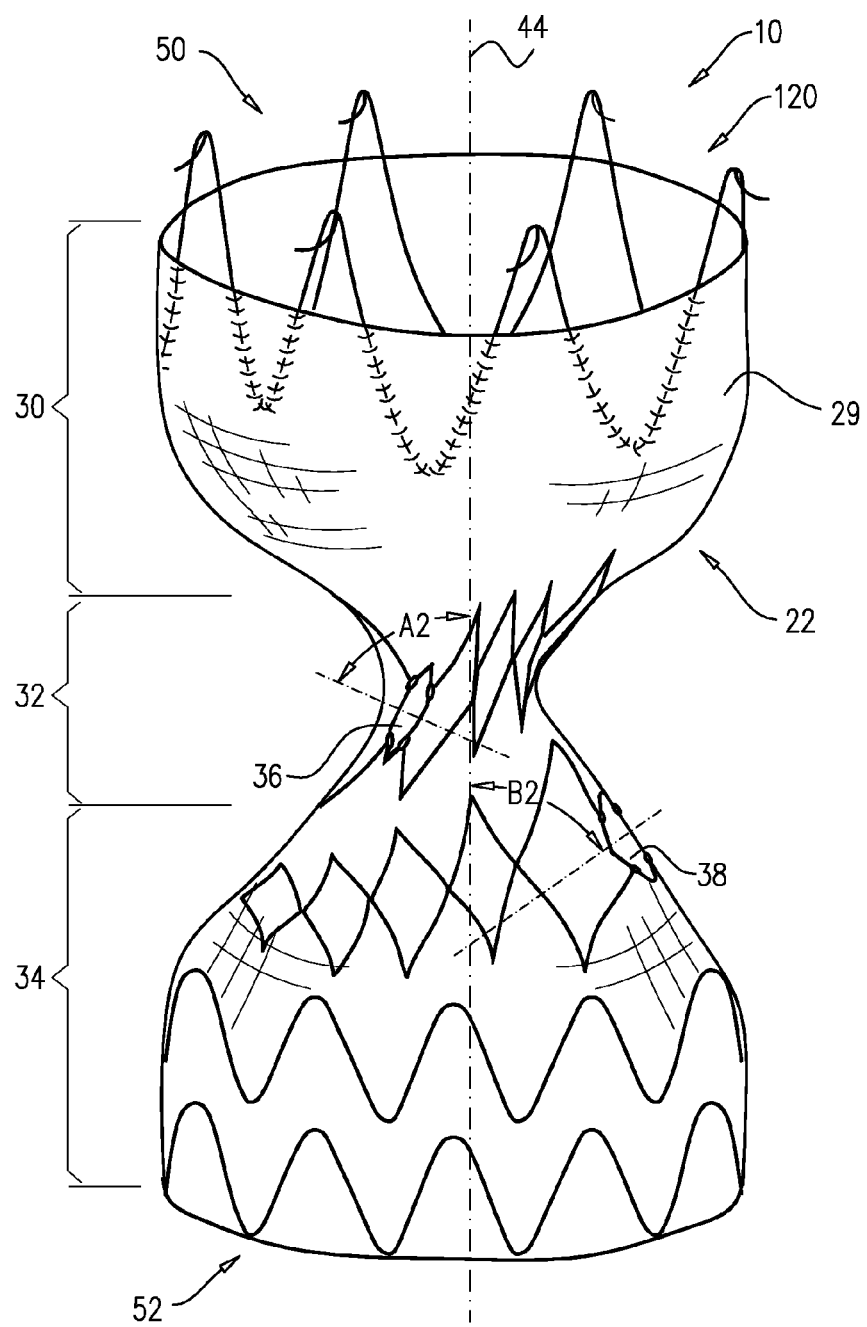
Figure 10C:
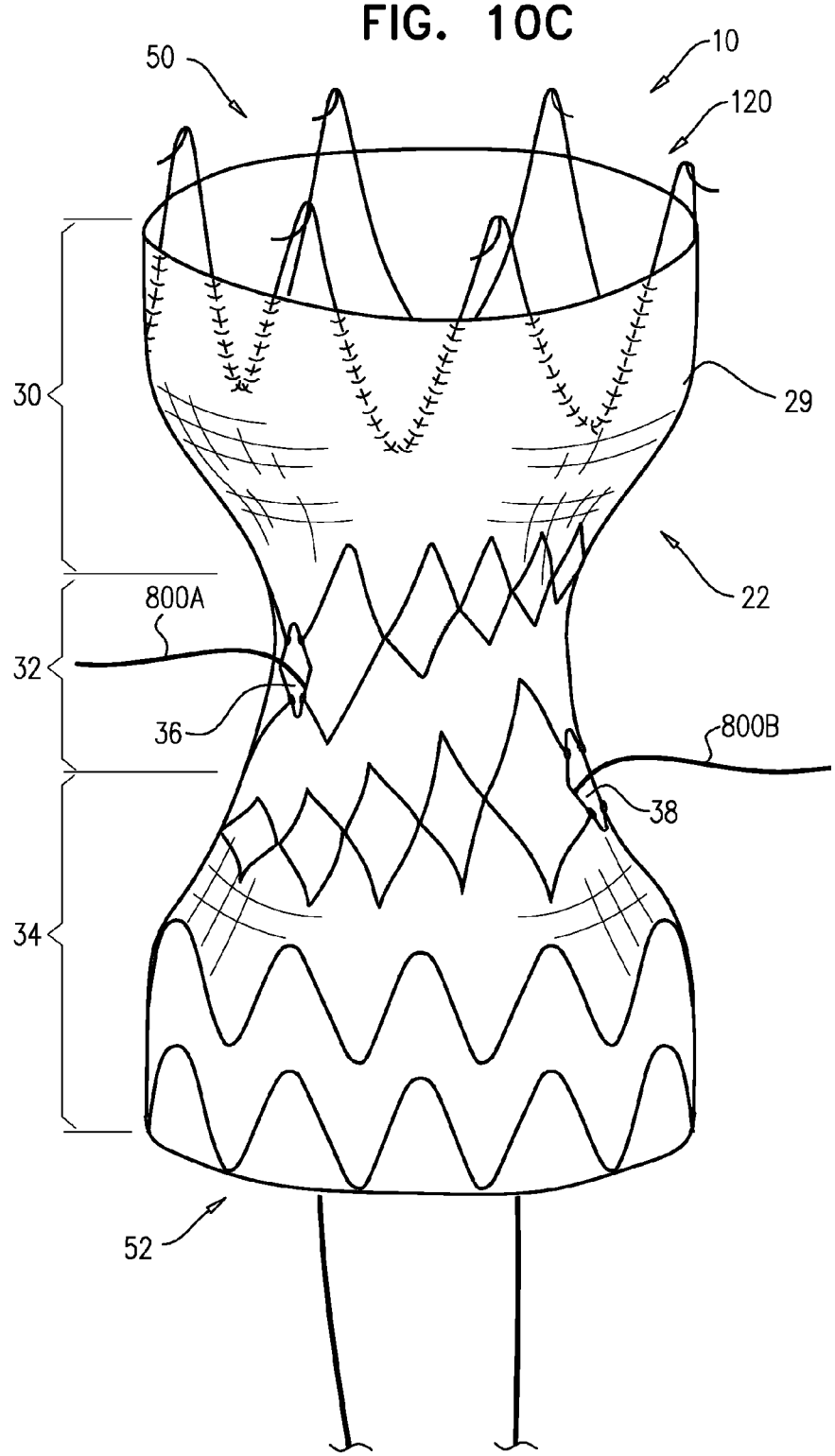

Reference is made to FIGS. 10A-C, which are schematic illustrations of a technique for deploying main stent-graft 10 and branching stent-grafts 500, in accordance with an application of the present invention. Although the stent elements of waist portion 32 are shown with the configuration of main stent-graft 120, these stent elements may instead have the configuration of main stent-graft 20, or other configurations.

FIG. 10A shows main stent-graft 10 in an intermediate deployment configuration, in which the diameter of waist portion 32 has not fully expanded from the initial radially-compressed delivery configuration to the radially-expanded deployment configuration. Typically, when waist portion 32 is in this intermediate deployment configuration, the second average diameter of waist portion 32 is at least 10% less than when the hourglass-shaped body is in the radially-expanded deployment configuration. When in the intermediate deployment configuration, waist portion 32 defines an angle A2 between (a) a line perpendicular to a plane defined by first lateral aperture 36 and (b) central longitudinal axis 44, and an angle B2 between (a) a line perpendicular to a plane defined by second lateral aperture 38 and (b) central longitudinal axis 44. Angles A2 and B2 are less than similarly defined angles A1 and B1 when hourglass-shaped body 22, including waist portion 32 is in the fully radially-expanded deployment configuration, as labeled in FIG. 3. As a result, it is generally easier to advance guidewires through the lateral apertures, because the lateral apertures are less sideways-facing than in the fully radially-expanded state.

FIG. 10B shows the insertion of two guidewires 800A and 800B into second end 52 of the stent-graft and out of first and second lateral apertures 36 and 38, while the main stent-graft is in the intermediate deployment configuration.

FIG. 10C shows the main stent-graft after it has been released to the radially-expanded deployment configuration, with the two guidewires still passing through first and second lateral apertures 36 and 38. The guidewires are subsequently used to deploy branching stent-grafts 500 through first and second lateral apertures 36 and 38, such as described hereinbelow with reference to FIGS. 11C-D.

For some applications, a releasable latching mechanism is provided; for example, the structural stent elements of waist portion 32 may comprise the latching mechanism. The latching mechanism is configured to assume a latched state in which the mechanism confines the structural stent elements of waist portion 32 in the intermediate deployment configuration.

For some applications, the releasable latching mechanism is configured to effect a transition of waist portion 32 from the intermediate deployment configuration to the radially-expanded deployment configuration upon a triggering event. For some applications, the triggering event is an exertion of outward radial pressure inside the waist portion. For some applications, the releasable latching mechanism comprises a longitudinal latching shaft that passes along at least a portion of the central longitudinal axis. For example, the triggering event may be a generally axial translation of the longitudinal latching shaft, or a generally rotational translation of the longitudinal latching shaft. For some applications, the releasable latching mechanism is implemented using techniques described in PCT Publication WO 2012/104842, which is assigned to the assignee of the present application and is incorporated herein by reference, such as with reference to FIGS. 3A-5B thereof.

Reference is now made to FIGS. 11A-F, which are schematic illustrations of an exemplary method of deploying main stent-graft 10 and two branching stent-grafts 500 in the vicinity of a sub-renal (e.g., juxtarenal) abdominal aortic aneurysm 910 of an abdominal aorta, in accordance with an application of the present invention.

As shown in FIG. 11A, during a first stage of the implantation procedure, stent-graft 10 is deployed using an endovascular stent delivery tool 900, which typically comprises a delivery catheter 902, a distal tip 904, and a guidewire 906. Stent-graft 10 is initially positioned in delivery catheter 902, restrained in the radially-compressed delivery configuration in the stent-graft's delivery configuration by the catheter. Stent-graft 10 is transvascularly (typically percutaneously) introduced into the aorta, e.g., via one of iliac arteries 914A or 914B, while positioned in delivery catheter 902. In this exemplary deployment, delivery catheter 902 and distal tip 904 are advanced over guidewire 906 until the distal tip is positioned at or slightly above renal arteries 912A and 912B.

Figure 11B:
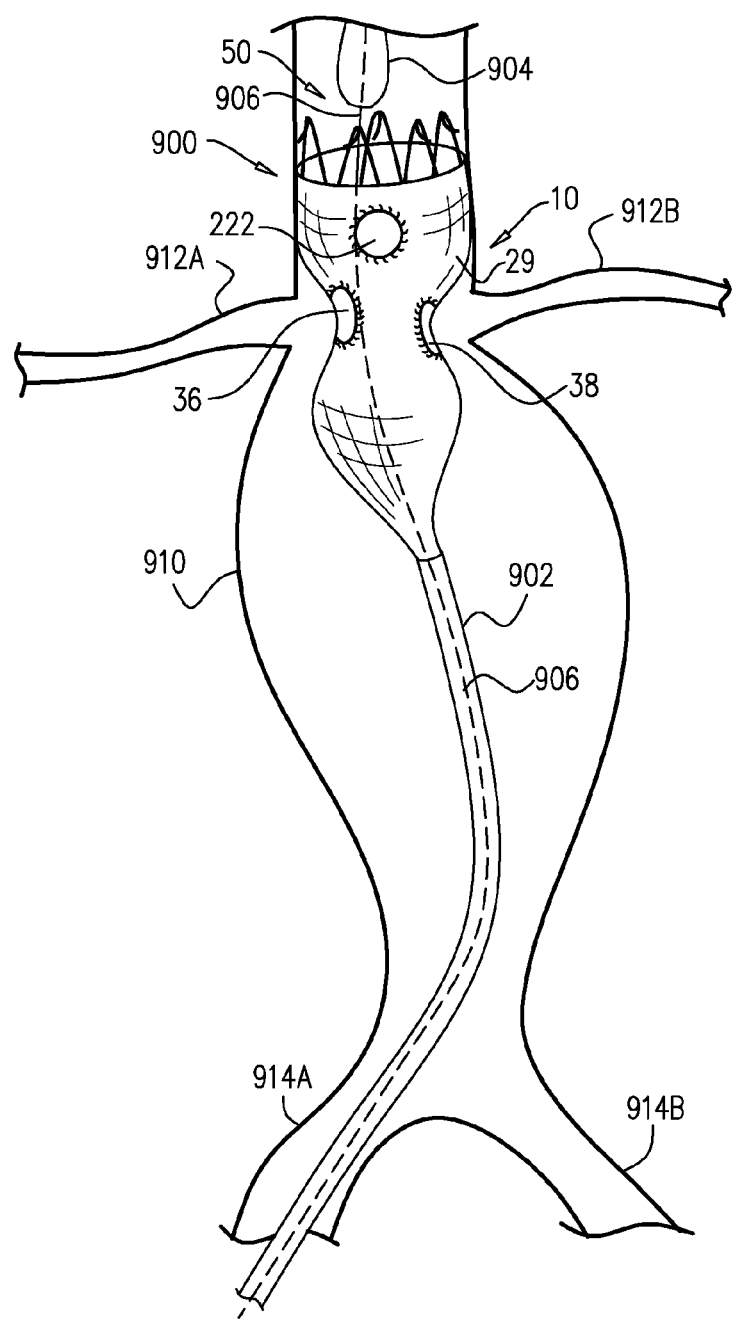

As shown in FIG. 11B, delivery catheter 902 is proximally withdrawn, releasing main stent-graft 10 in the aorta. The stent-graft radially expands and transitions to the radially-expanded deployment configuration as it is released, until first longitudinal portion 30 comes in contact with a wall of the blood vessel, e.g., a wall of the aorta above the renal arteries in this exemplary deployment.

Figure 11C:
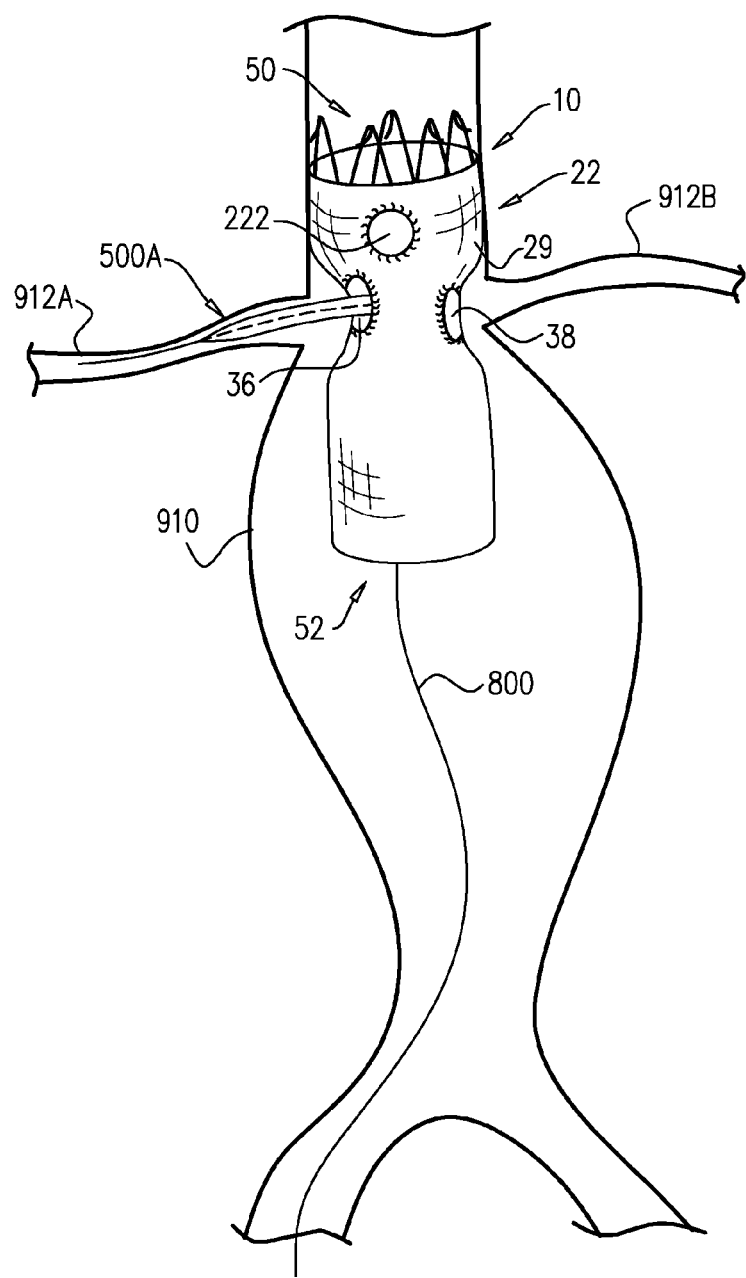

As shown in FIG. 11C, a guidewire 800 is introduced through second end 52 of the stent-graft, out of first lateral aperture 36, and into right renal artery 912A. A first branching stent-graft 500A is introduced over guidewire 800 while the branching stent-graft is in a radially-compressed delivery configuration in a delivery catheter. Optionally, a second guidewire 800 is introduced before the first branching stent-graft is introduced. Optionally, during the introduction of one or both guidewires 800, main stent-graft 10 is only partially expanded to the intermediate deployment configuration, as described hereinabove with reference to FIGS. 10A-C.

For applications in which radiopaque markers 70 or radiopaque wires 440, 442, 444, and/or 446 are provided, such as described hereinabove with reference to FIG. 2 and FIG. 7, respectively, the radiopaque markers aid the surgeon during insertion of the guiding catheters, and/or guidewires, and/or subsequently, the branching stent-grafts into the lateral apertures.

Figure 11D:
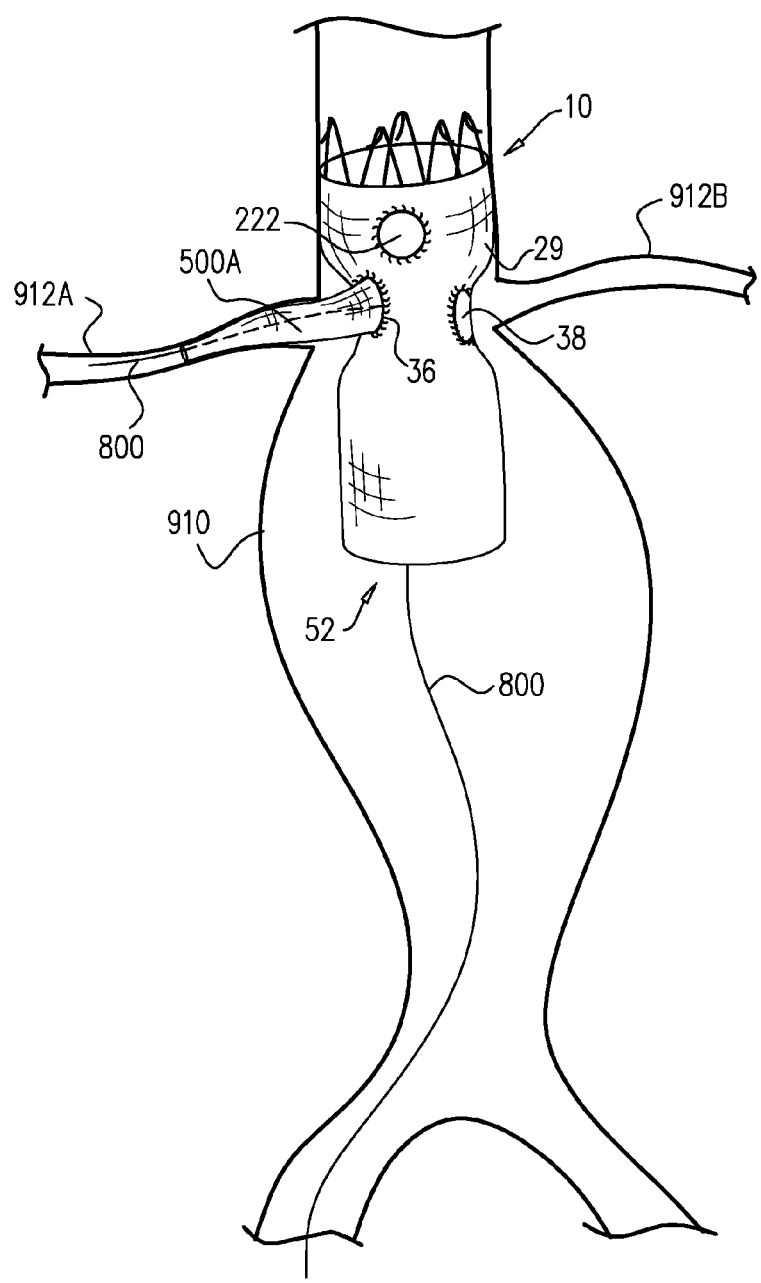

As shown in FIG. 11D, the surgeon withdraws the delivery catheter of first branching stent-graft 500A, thereby releasing the first branching stent-graft within right renal artery 912A, such that interface portion 542 of the branching stent-graft engages and forms a blood-tight seal with first lateral aperture 36. Guidewire 800 is then removed.

Figure 11E:
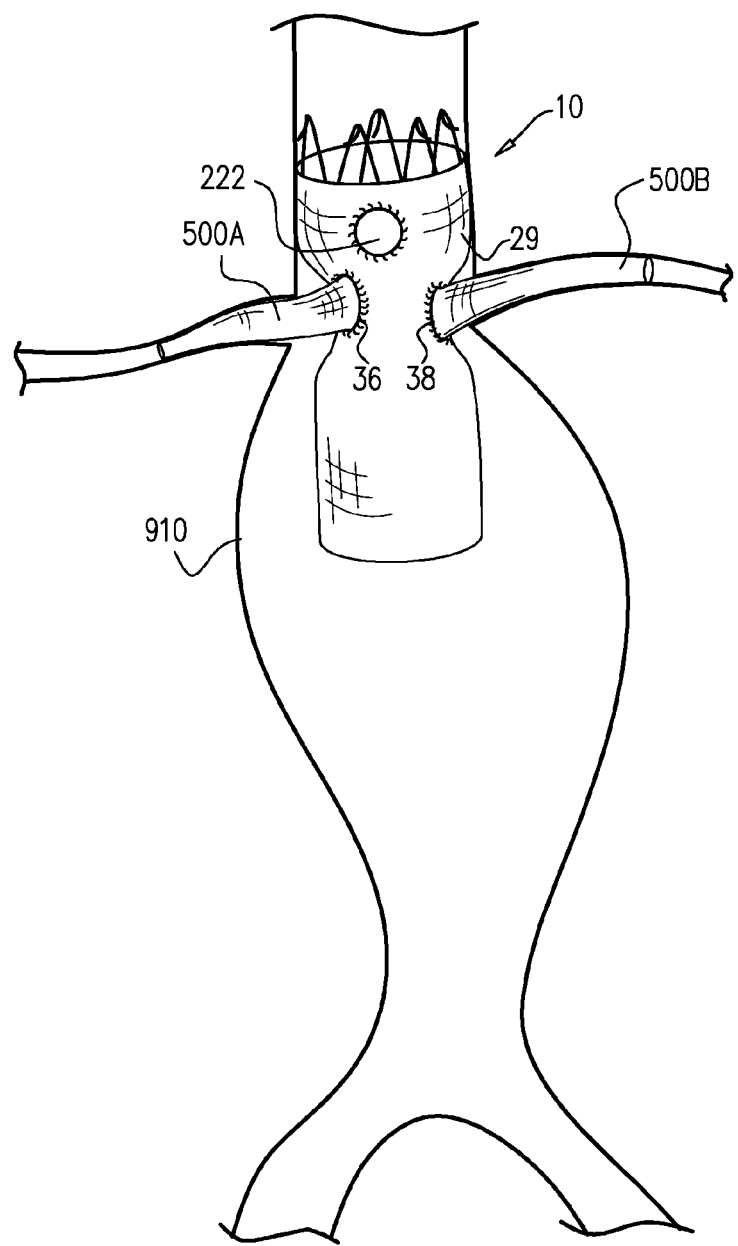

As shown in FIG. 11E, a second branching stent-graft 500B is deployed in left renal artery 912B, using the techniques described above with reference to FIGS. 11C-D.

For some applications, an endovascular angioplasty balloon is provided, which comprises a proximal lobe and a distal lobe and a radiopaque marker positioned therebetween. The proximal and distal lobes of the balloon are sized to be expandable to at least 10% greater than a greater of (a) a diameter the first lateral aperture and (b) a diameter of the second lateral aperture. The balloon is inflated inside the main stent-graft after the branching stent-grafts have been deployed, so as to minimize and homogeneously distribute folds of fabric 29 around the circumference of the main stent-graft. The two lobes are provided in order to avoid crushing the portions of the branching stent-grafts that are within waist portion 32. The balloon is thus sized such that the proximal and distal lobes correspond in longitudinal dimensions with first and second longitudinal portions 30 and 34, respectively.

Figure 11F:
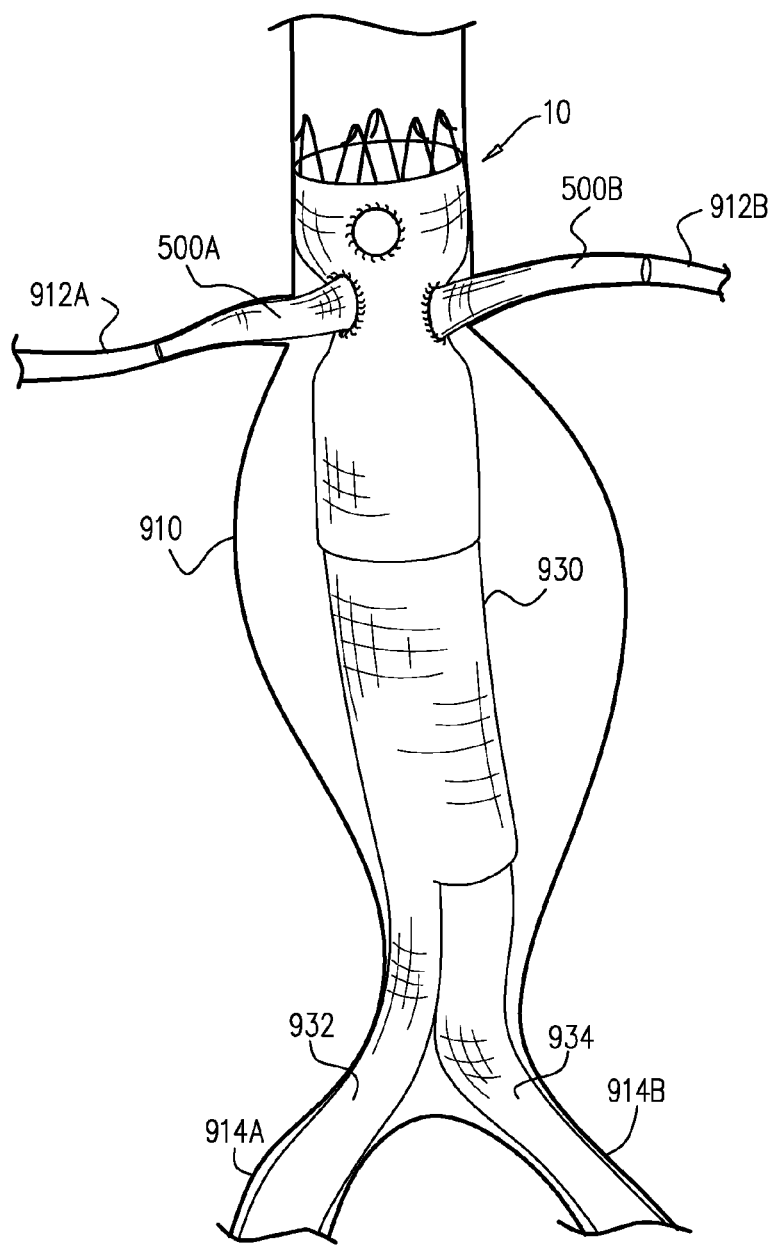

As shown in FIG. 11F, one or more additional stent-grafts are coupled to main stent-graft 10, in order to provide one or more continuous blood-flow lumens through aortic aneurysm 910 to iliac arteries 914A and 914B. The stent-grafts are coupled together to form substantially blood impervious seals. Second longitudinal portion 34 of the main stent-graft may positioned inside the other stent-graft, or the other stent-graft may positioned inside the second longitudinal portion of the main stent-graft.

In the particular configuration shown in FIG. 11F, a primary stent-graft 930 is deployed in the descending aorta with a branch 932 there of positioned in one of the iliac arteries, and a secondary stent-graft 934 is coupled to the primary stent-graft and positioned in the other of the iliac arteries.

As a result, blood flows into first end 50 of main stent-graft 10 and feeds both iliac arteries, as well as the renal arteries and, optionally, the superior mesenteric artery (SMA) and celiac artery.

Figure 12:
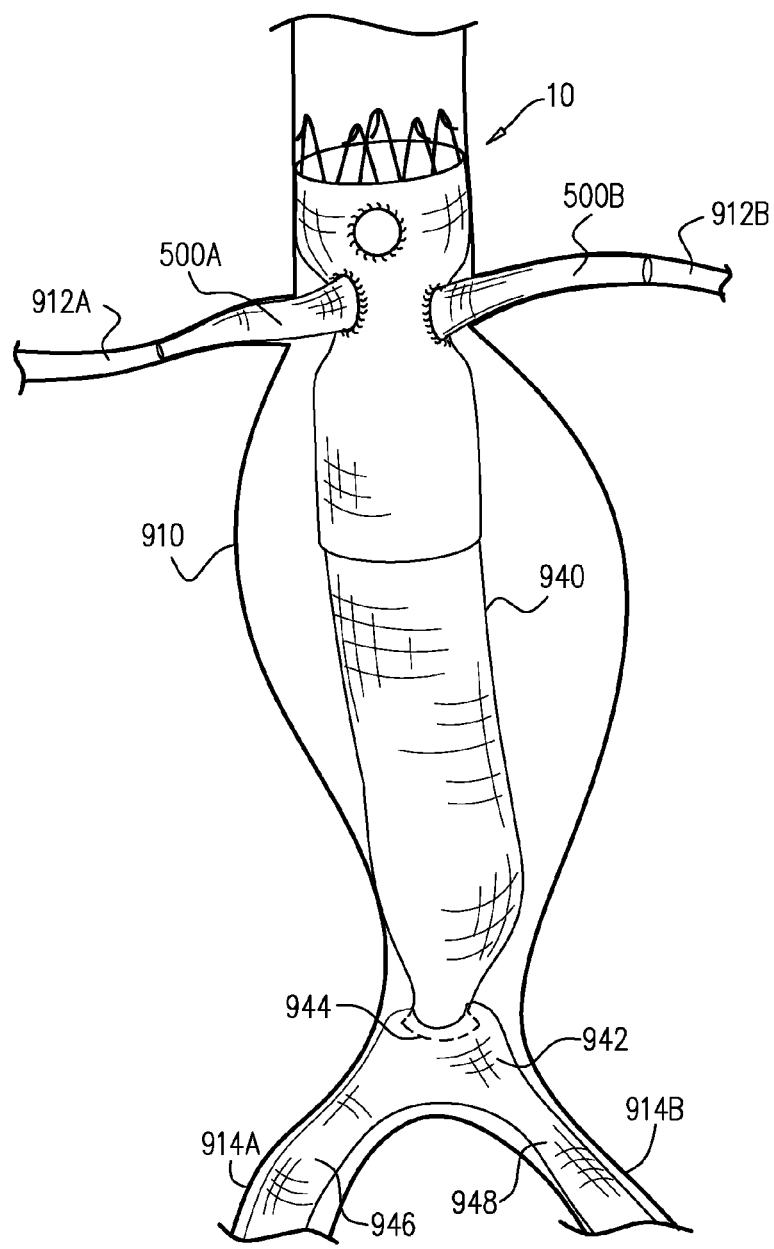
FIG. 12 is a schematic illustration of an alternative deployment of the main stent-graft and accompanying stent-grafts, in accordance with an application of the present invention.

Reference is made to FIG. 12, which is a schematic illustration of an alternative deployment of main stent-graft 10 and accompanying stent-grafts, in accordance with an application of the present invention. This deployment is similar to that of FIG. 11F, except that a stent-graft 942 is deployed in the iliac arteries, spanning the aorto-iliac junction, with legs 946 and 948 of the stent-graft in respective iliac arteries. A vertical stent-graft 940 is coupled to main stent-graft 10 and an aorta-facing aperture of stent-graft 942. This configuration may be practiced in combination with techniques described in PCT Publication WO 2011/007354, which is assigned to the assignee of the present application and is incorporated herein by reference.

The techniques described with reference to FIGS. 11A-F may be used, for example, to deploy:

the main stent-graft in the aortic arch, and one or more branching stent-grafts in the brachiocephalic artery, the left common carotid artery, and/or the left subclavian artery 105; for example, for treating TAA, the main stent-graft may be shaped so as to define the primary and secondary superior apertures (and typically not define the scallop), and first longitudinal portion 30 may be as long as required, as there are no other major branching vessels in the thoracic aorta, until the arch begins; the secondary superior aperture is positioned adjacent the celiac artery, the primary superior aperture adjacent the SMA, and the lateral apertures facing the renal arteries.

the main stent-graft in the common iliac artery at the bifurcation of the common iliac artery to the internal iliac artery, and one or more branching stent-grafts in the internal iliac artery and/or external iliac artery;

the main stent-graft in the superficial femoral artery (SFA) at the bifurcation of iliac artery to the SFA and to the deep femoral artery, and a branching stent-graft in the femoral circumflex; or the main stent-graft spanning the common carotid and the internal carotid at the carotid bifurcation to the internal and external carotid arteries, and a branching stent-graft in the external carotid.

As used in the present application, including in the claims, "tubular" means having the form of an elongated hollow object that defines a conduit therethrough. A "tubular" structure may have varied cross-sections therealong, and the cross-sections are not necessarily circular. For example, one or more of the cross-sections may be generally circular, or generally elliptical but not circular, or circular.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

PCT Application PCT/IL2008/000287, filed Mar. 5, 2008, which published as PCT Publication WO 2008/107885 to Shalev et al., and U.S. application Ser. No. 12/529,936 in the national stage thereof, which published as US Patent Application Publication 2010/0063575 to Shalev et al.

U.S. Provisional Application 60/892,885, filed Mar. 5, 2007

U.S. Provisional Application 60/991,726, filed Dec. 2, 2007

U.S. Provisional Application 61/219,758, filed Jun. 23, 2009

U.S. Provisional Application 61/221,074, filed Jun. 28, 2009

PCT Application PCT/IB2010/052861, filed Jun. 23, 2010, which published as PCT Publication WO 2010/150208

PCT Application PCT/IL2010/000564, filed Jul. 14, 2010, which published as PCT Publication WO 2011/007354

PCT Application PCT/IL2010/000917, filed Nov. 4, 2010, which published as PCT Publication WO 2011/055364

PCT Application PCT/IL2010/000999, filed Nov. 30, 2010, which published as PCT Publication WO 2011/064782

PCT Application PCT/IL2010/001018, filed Dec. 2, 2010, which published as PCT Publication WO 2011/067764

PCT Application PCT/IL2010/001037, filed Dec. 8, 2010, which published as PCT Publication WO 2011/070576

PCT Application PCT/IL2011/000135, filed Feb. 8, 2011, entitled, "Thermal energy application for prevention and management of endoleaks in stent-grafts," which published as PCT Publication WO 2011/095979

U.S. application Ser. No. 13/031,871, filed Feb. 22, 2011, entitled, "Flexible stent-grafts," which published as US Patent Application Publication 2011/0208289

U.S. Provisional Application 61/496,613, filed Jun. 14, 2011

U.S. Provisional Application 61/505,132, filed Jul. 7, 2011

U.S. Provisional Application 61/529,931, filed Sep. 1, 2011

PCT Application PCT/IL2012/000060, filed Feb. 2, 2012, which published as PCT Publication WO 2012/104842

PCT Application PCT/IL2012/000083, filed Feb. 16, 2012, which published as PCT Publication WO 2012/111006

PCT Application PCT/IL2012/000095, filed Mar. 1, 2012, which published as PCT Publication WO 2012/117395

PCT Application PCT/IL2012/000148, filed Apr. 4, 2012, entitled, "Stent-grafts with post-deployment variable axial and radial displacement," which published as PCT Publication WO 2013/030818

PCT Application PCT/IL2012/000190, filed May 15, 2012, entitled, "Stent-graft with fixation elements that are radially confined for delivery," which published as PCT Publication WO 2013/171730

U.S. patent application Ser. No. 13/523,296, filed Jun. 14, 2012, which issued as U.S. Pat. No. 8,574,287

PCT Application PCT/IL2012/000241, filed Jun. 19, 2012, entitled, "Endovascular system with circumferentially-overlapping stent-grafts," which published as PCT Publication WO 2012/176187

PCT Application PCT/IL2012/000269, filed Jul. 2, 2012, entitled, "Stent fixation with reduced plastic deformation," which published as PCT Publication WO 2013/005207

PCT Application PCT/IL2012/050424, filed Oct. 29, 2012, entitled, "Triple-collar stent-graft," which published as PCT Publication WO 2013/065040

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising an endovascular stent-graft, which (a) is configured to assume a radially-compressed delivery configuration and a radially-expanded deployment configuration, and (b) comprises a generally tubular hourglass-shaped body, which comprises:
   a flexible stent member, which comprises a plurality of structural stent elements; and
   a tubular fluid flow guide, which comprises a fabric, and is attached to the structural stent elements,
   wherein, when the stent-graft is in the radially-expanded deployment configuration, the hourglass-shaped body is shaped so as to define a narrow waist portion longitudinally surrounded by and adjacent to wider first and second longitudinal portions of the hourglass-shaped body,
   wherein the fabric along the narrow waist portion is shaped so as to define at least first and second lateral apertures, and
   wherein the stent-graft, including the hourglass-shaped body, including the narrow waist portion, is configured to assume an intermediate deployment configuration, in which (a) the hourglass-shaped body is shaped so as to define the narrow waist portion surrounded by and adjacent to the wider first and second longitudinal portions, and (b) an average diameter of the narrow waist portion is at least 10% less than when the stent-graft, including the hourglass-shaped body, including the narrow waist portion, is in the radially-expanded deployment configuration.

2. The apparatus according to claim 1, further comprising an endovascular angioplasty balloon comprising a proximal lobe and a distal lobe and a radiopaque marker positioned therebetween, wherein the proximal and distal lobes of the balloon are sized to be expandable to at least 10% greater than a greater of (a) a diameter of the first lateral aperture and (b) a diameter of the second lateral aperture.

3. The apparatus according to claim 1, wherein the apparatus further comprises a releasable latching mechanism, which is configured to assume a latched state in which the mechanism confines the structural stent elements of the narrow waist portion in the intermediate deployment configuration.

4. The apparatus according to claim 3, wherein the releasable latching mechanism is configured to effect a transition of the narrow waist portion from the intermediate deployment configuration to the radially-expanded deployment configuration upon a triggering event.

5. The apparatus according to claim 4, wherein the triggering event is an exertion of outward radial pressure inside the narrow waist portion.

6. The apparatus according to claim 4, wherein the releasable latching mechanism comprises a longitudinal latching shaft that passes along at least a portion of a central longitudinal axis of the hourglass-shaped body, and wherein the triggering event is a generally axial translation of the longitudinal latching shaft.

7. The apparatus according to claim 4, wherein the releasable latching mechanism comprises a longitudinal latching shaft that passes along at least a portion of a central longitudinal axis of the hourglass-shaped body, and wherein the triggering event is a generally rotational translation of the longitudinal latching shaft.

8. The apparatus according to claim 1, wherein the fabric along the first longitudinal portion is shaped so as to define at least one superior scallop, the superior scallop being characterized by a width and a height, when the stent-graft, including the hourglass-shaped body, is in the radially-expanded deployment configuration.

9. The apparatus according to claim 8, wherein the superior scallop is disposed so as to define a superior scallop arc angle around a central longitudinal axis of the hourglass-shaped body between (a) a center of the superior scallop and (b) a midpoint of an arc angle between respective centers of the first and the second lateral apertures, the superior scallop arc angle being less than 60 degrees when the stent-graft, including the hourglass-shaped body, is in the radially-expanded deployment configuration.

10. The apparatus according to claim 8, wherein the width of the superior scallop is between 5 and 12 mm.

11. The apparatus according to claim 8, wherein the height of the superior scallop is between 5 and 25 mm.

12. The apparatus according to claim 1,
wherein, when the stent-graft, including the hourglass-shaped body, including the narrow waist portion, is in the radially-expanded deployment configuration, the narrow waist portion defines a first angle between (a) a line perpendicular to a plane defined by the first lateral aperture and (b) a central longitudinal axis of the hourglass-shaped body,
wherein, when the stent-graft, including the hourglass-shaped body, including the narrow waist portion, is in the intermediate deployment configuration, the narrow waist portion defines a second angle between (a) a line perpendicular to a plane defined by the first lateral aperture and (b) the central longitudinal axis, and
wherein the second angle is less than the first angle.

13. The apparatus according to claim 1, wherein the first and the second lateral apertures are less sideways-facing when the stent-graft, including the hourglass-shaped body, including the narrow waist portion, is in the intermediate deployment configuration than when the stent-graft, including the hourglass-shaped body, including the narrow waist portion, is in the radially-expanded deployment configuration.

14. The apparatus according to claim 1, wherein greatest respective diameters of the first and the second longitudinal portions of the hourglass-shaped body remain constant (a) when the stent-graft, including the hourglass-shaped body, including the narrow waist portion, is in the radially-expanded deployment configuration, and (b) when the stent-graft, including the hourglass-shaped body, including the narrow waist portion, is in the intermediate deployment configuration.

15. A method comprising:
providing an endovascular stent-graft, which includes a generally tubular hourglass-shaped body, which includes (a) a flexible stent member, which includes a plurality of structural stent elements, and (b) a tubular fluid flow guide, which comprises a fabric, and is attached to the structural stent elements;
transvascularly introducing the stent-graft into a blood vessel of a human subject while the stent-graft, including the hourglass-shaped body, is in a radially-compressed delivery configuration;
thereafter, transitioning the stent-graft, including the hourglass-shaped body, to an intermediate deployment configuration, in which the hourglass-shaped body is shaped so as to define a narrow waist portion longitudinally surrounded by and adjacent to wider first and second longitudinal portions of the hourglass-shaped body, and the fabric along the second portion is shaped so as to define at least first and second lateral apertures; and
thereafter, transitioning the stent-graft, including the hourglass-shaped body, to a radially-expanded deployment configuration in the blood vessel, in which radially-expanded configuration the hourglass-shaped body is shaped so as to define the narrow waist portion longitudinally surrounded by and adjacent to the wider first and second longitudinal portions, and the fabric along the second portion is shaped so as to define at least the first and the second lateral apertures,
wherein, when the stent-graft, including the hourglass-shaped body, including the narrow waist portion, is in the intermediate deployment configuration, an average diameter of the narrow waist portion is at least 10% less than when the stent-graft, including the hourglass-shaped body, including the narrow waist portion, is in the radially-expanded deployment configuration.

16. The method according to claim 15,
wherein the method further comprises inserting first and second guidewires into the stent-graft and out of the first and the second lateral apertures, respectively, while the stent-graft, including the hourglass-shaped body, including the narrow waist portion, is in the intermediate deployment configuration,
wherein transitioning the stent-graft, including the hourglass-shaped body, to the radially-expanded deployment configuration comprises transitioning the stent-graft, including the hourglass-shaped body, to the radially-expanded deployment configuration with the first and the second two guidewires still passing through the first and the second lateral apertures, and wherein the method further comprises subsequently deploying first and second branching stent-grafts through the first and the second lateral apertures, respectively, using the first and the second guidewires, respectively.

17. The method according to claim 15, wherein, when the stent-graft, including the hourglass-shaped body, including the narrow waist portion, is in the radially-expanded deployment configuration, the narrow waist portion defines a first angle between (a) a line perpendicular to a plane defined by the first lateral aperture and (b) a central longitudinal axis of the hourglass-shaped body, wherein, when the stent-graft, including the hourglass-shaped body, including the narrow waist portion, is in the intermediate deployment configuration, the narrow waist portion defines a second angle between (a) a line perpendicular to a plane defined by the first lateral aperture and (b) the central longitudinal axis, and wherein the second angle is less than the first angle.

18. The method according to claim 15, wherein the first and the second lateral apertures are less sideways-facing when the stent-graft, including the hourglass-shaped body, including the narrow waist portion, is in the intermediate deployment configuration than when the stent-graft, including the hourglass-shaped body, including the narrow waist portion, is in the radially-expanded deployment configuration.

19. The method according to claim 15, wherein greatest respective diameters of the first and the second longitudinal portions of the hourglass-shaped body remain constant (a) when the stent-graft, including the hourglass-shaped body, including the narrow waist portion, is in the radially-expanded deployment configuration, and (b) when the stent-graft, including the hourglass-shaped body, including the narrow waist portion, is in the intermediate deployment configuration.

20. The method according to claim 15, wherein transitioning the stent-graft, including the hourglass-shaped body, to the intermediate deployment configuration comprises providing a releasable latching mechanism in a latched state in which the mechanism confines the structural stent elements of the narrow waist portion in the intermediate deployment configuration.

21. The method according to claim 20, wherein transitioning the stent-graft, including the hourglass-shaped body, to the radially-expanded deployment configuration comprises triggering the releasable latching mechanism to effect a transition of the narrow waist portion from the intermediate deployment configuration to the radially-expanded deployment configuration.

22. The method according to claim 21, wherein triggering the releasable latching mechanism comprises exerting outward radial pressure inside the narrow waist portion.

23. The method according to claim 21, wherein the releasable latching mechanism includes a longitudinal latching shaft that passes along at least a portion of a central longitudinal axis of the hourglass-shaped body, and wherein triggering the releasable latching mechanism comprises generally axially translating the longitudinal latching shaft.

24. The method according to claim 21, wherein the releasable latching mechanism includes a longitudinal latching shaft that passes along at least a portion of a central longitudinal axis of the hourglass-shaped body, and wherein triggering the releasable latching mechanism comprises generally rotationally translating the longitudinal latching shaft.

25. The method according to claim 15, further comprising, after transitioning the stent-graft, including the hourglass-shaped body, to the radially-expanded deployment configuration, inflating, inside the stent-graft, an endovascular angioplasty balloon that includes a proximal lobe and a distal lobe and a radiopaque marker positioned therebetween, wherein the proximal and distal lobes of the balloon are sized to be expandable to at least 10% greater than a greater of (a) a diameter of the first lateral aperture and (b) a diameter of the second lateral aperture.

26. The method according to claim 15, wherein the fabric along the first longitudinal portion is shaped so as to define at least one superior scallop, the superior scallop being characterized by a width and a height, when the stent-graft, including the hourglass-shaped body, is in the radially-expanded deployment configuration.

27. The method according to claim 26, wherein the superior scallop is disposed so as to define a superior scallop arc angle around a central longitudinal of the hourglass-shaped body axis between (a) a center of the superior scallop and (b) a midpoint of an arc angle between respective centers of the first and the second lateral apertures, the superior scallop arc angle being less than 60 degrees when the stent-graft, including the hourglass-shaped body, is in the radially-expanded deployment configuration.

28. The method according to claim 26, wherein the width of superior scallop is between 5 and 12 mm.

29. The method according to claim 26, wherein the height of superior scallop is between 5 and 25 mm.

* * * * *